US012478373B2

(12) United States Patent
Cooper et al.

(10) Patent No.: US 12,478,373 B2
(45) Date of Patent: Nov. 25, 2025

(54) STAPLER RELOAD ASSEMBLIES AND RELATED DEVICES, SYSTEMS, AND METHODS

(71) Applicant: INTUITIVE SURGICAL OPERATIONS, INC., Sunnyvale, CA (US)

(72) Inventors: Emily Cooper, San Francisco, CA (US); Heath Corbet, Campbell, CA (US); Austin C. de Maillé, Manhattan, MT (US); Babak D. Jasemian, Trabuco Canyon, CA (US); Donald F. Wilson, Jr., Trumbull, CT (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 0 days.

(21) Appl. No.: 18/261,935

(22) PCT Filed: Jan. 18, 2022

(86) PCT No.: PCT/US2022/012728

§ 371 (c)(1),
(2) Date: Jul. 18, 2023

(87) PCT Pub. No.: WO2022/159369

PCT Pub. Date: Jul. 28, 2022

(65) Prior Publication Data

US 2024/0299029 A1 Sep. 12, 2024

Related U.S. Application Data

(60) Provisional application No. 63/139,081, filed on Jan. 19, 2021.

(51) Int. Cl.
*A61B 17/072* (2006.01)
*A61B 17/00* (2006.01)

(52) U.S. Cl.
CPC .................. *A61B 17/07207* (2013.01); *A61B 2017/00477* (2013.01); *A61B 2017/07271* (2013.01)

(58) Field of Classification Search
CPC ................ A61B 17/068; A61B 17/072; A61B 2017/07207; A61B 2017/07271;
(Continued)

(56) References Cited

U.S. PATENT DOCUMENTS 5,366,133 A 11/1994 Geiste
8,397,972 B2 3/2013 Kostrzewski
(Continued)

FOREIGN PATENT DOCUMENTS

CA 2188738 A1 4/1997
EP 0178942 A2 4/1986
(Continued)

OTHER PUBLICATIONS

Extended European Search Report for Application No. EP20200762473, mailed on Oct. 24, 2022, 11 pages.
(Continued)

*Primary Examiner* — Anna K Kinsaul
*Assistant Examiner* — Linda J. Hodge
(74) *Attorney, Agent, or Firm* — Jones Robb, PLLC

(57) ABSTRACT

A stapler reload assembly includes a cartridge body. The cartridge body comprises a plurality of staple apertures configured to eject staples housed in the cartridge body and a staple retainer removably coupled to the cartridge body. The staple retainer comprises a main body portion configured to at least partially cover the plurality of staple apertures in a position of the staple retainer coupled to the cartridge body, a first handling portion extending from the main body portion at a distal end portion of the staple retainer, and a second handling portion proximal the first
(Continued)

handling portion and coupled to the main body portion by a flexure. The second handling portion is elastically deflectable about the flexure and relative to the main body portion of the staple retainer from a neutral, first position to a deflected second position. Devices and methods relate to stapler reload assemblies.

18 Claims, 36 Drawing Sheets

(58) Field of Classification Search
CPC .... A61B 17/07292; A61B 2017/00477; A61B 17/105; A61B 2017/0688; A61B 90/03; A61B 2090/038
USPC .......................................................... 227/176.1
See application file for complete search history.

(56) References Cited

U.S. PATENT DOCUMENTS

| | | | | |
|---|---|---|---|---|
| 8,852,174 | B2 | 10/2014 | Burbank | |
| 8,876,857 | B2 | 11/2014 | Burbank | |
| 8,991,678 | B2 | 3/2015 | Wellman et al. | |
| 9,004,339 | B1 | 4/2015 | Park | |
| 9,259,275 | B2 | 2/2016 | Burbank | |
| 9,924,941 | B2 | 3/2018 | Burbank et al. | |
| 12,064,110 | B2 | 8/2024 | De et al. | |
| 2004/0007608 | A1 | 1/2004 | Ehrenfels et al. | |
| 2005/0222616 | A1 | 10/2005 | Rethy et al. | |
| 2006/0151569 | A1 | 7/2006 | Ehrenfels et al. | |
| 2009/0134200 | A1 | 5/2009 | Tarinelli et al. | |
| 2012/0080491 | A1 | 4/2012 | Shelton, IV et al. | |
| 2012/0145714 | A1 | 6/2012 | Farascioni et al. | |
| 2012/0241499 | A1* | 9/2012 | Baxter, III | A61B 17/0644 227/176.1 |
| 2013/0068816 | A1 | 3/2013 | Mandakolathur Vasudevan et al. | |
| 2013/0105552 | A1 | 5/2013 | Weir et al. | |
| 2013/0146642 | A1 | 6/2013 | Shelton, IV et al. | |
| 2013/0153641 | A1 | 6/2013 | Shelton, IV et al. | |
| 2013/0240599 | A1 | 9/2013 | Scirica | |
| 2014/0224686 | A1* | 8/2014 | Aronhalt | A61B 17/0682 206/339 |
| 2014/0252065 | A1 | 9/2014 | Hessler et al. | |
| 2015/0297227 | A1* | 10/2015 | Huitema | A61B 17/0644 227/177.1 |
| 2017/0265864 | A1* | 9/2017 | Hessler | A61B 17/07207 |
| 2017/0290584 | A1 | 10/2017 | Jasemian et al. | |
| 2018/0168586 | A1* | 6/2018 | Shelton, IV | A61B 17/072 |
| 2018/0235626 | A1 | 8/2018 | Shelton, IV et al. | |
| 2018/0250000 | A1 | 9/2018 | Hodgkinson et al. | |
| 2019/0015101 | A1* | 1/2019 | Matthias | A61B 17/07207 |
| 2019/0038371 | A1 | 2/2019 | Wixey et al. | |
| 2019/0053801 | A1 | 2/2019 | Wixey et al. | |
| 2020/0261075 | A1 | 8/2020 | Boudreaux et al. | |
| 2020/0261076 | A1 | 8/2020 | Boudreaux et al. | |
| 2020/0405301 | A1* | 12/2020 | Shelton, IV | A61B 17/1155 |
| 2022/0142642 | A1 | 5/2022 | De et al. | |
| 2023/0277172 | A1* | 9/2023 | Chang | A61B 17/07207 227/176.1 |

FOREIGN PATENT DOCUMENTS

| | | | |
|---|---|---|---|
| WO | WO-2018049198 | A1 | 3/2018 |
| WO | WO-2018049206 | A1 | 3/2018 |
| WO | WO-2018049211 | A1 | 3/2018 |
| WO | WO-2018071497 | A1 | 4/2018 |
| WO | WO-2020081960 | A1 | 4/2020 |
| WO | WO-2020131685 | A1 | 6/2020 |
| WO | WO-2020131692 | A1 | 6/2020 |
| WO | WO-2020176557 | A1 | 9/2020 |
| WO | WO-2020214397 | A1 | 10/2020 |

OTHER PUBLICATIONS

International Search Report and Written Opinion for Application No. PCT/US2020/019785, mailed Jun. 22, 2020, 18 pages.
Renewing Hook and Loop Fasteners—Velcro (R) Brand Fasteners—video presentation by DirtFarmer Jay (hereinafter "DFJ"). Retrieved from URL https://www.youtube.com/watchv=dFR2DYU1lgk (Year: 2015), 03 pages.
Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.
Extended European Search Report for European Application No. EP25159504 dated Apr. 29, 2025, 14 pages.

* cited by examiner

STAPLER RELOAD ASSEMBLIES AND RELATED DEVICES, SYSTEMS, AND METHODS

CROSS-REFERENCE TO RELATED APPLICATIONS

This application is a U.S. national stage application under 35 U.S.C. § 371(c) of International PCT Application No. PCT/US2022/012728, filed Jan. 18, 2022, which claims the benefit of priority to U.S. Provisional Patent Application No. 63/139,081, filed Jan. 19, 2021 and titled STAPLER RELOAD ASSEMBLIES AND RELATED DEVICES, SYSTEMS, AND METHODS, the entire contents of which are incorporated by reference herein.

This application is related to International Patent Application Publication No. WO2020/176557, filed Feb. 26, 2020 and titled STAPLER RELOAD ASSEMBLIES AND RELATED DEVICES, SYSTEMS, AND METHODS.

TECHNICAL FIELD

Aspects of the present disclosure relate to stapler reload assemblies, such as for surgical staplers, and related devices, systems, and methods.

INTRODUCTION

It is often a design objective to make endoscopic instruments smaller so that procedures in which endoscopic instruments are used can be less invasive. An example of such endoscopic instruments includes stapler instruments and their associated reload assemblies. A competing consideration when reducing a size of the stapler instrument and reload assembly, however, is the size of staples the instrument can accept and fire. That is, the transverse (perpendicular to a longitudinal or length direction of the stapler head) cross-sectional dimensions (e.g., diameter or other lateral dimension) of the stapler instrument and reload assembly constrain the maximum size (e.g., width and height) of staples the instrument can accept. Reload assemblies typically include one or more components that retain the staples and other parts of the reload assembly in place during manufacture, shipping, and installation of the reload assembly. Such components contribute to the overall size (e.g., transverse cross-sectional dimensions) of the reload assembly, and correspondingly constrain the maximum size of staples that can be accepted and fired by a stapler instrument in which the reload assembly is used.

There exists a need to provide stapler instruments, and in particular their reload assemblies, that have relatively small transverse cross-sectional dimensions while still being able to accept relatively large staple sizes. In other words, there exists a need to provide a stapler instrument design with an overall reduced size in terms of its transverse cross-sectional dimensions, without unduly limiting the size of the staple that can be accepted and fired by the endoscopic stapler instrument.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, a stapler reload assembly includes a cartridge body defining a housing to receive staples. The cartridge body comprises a plurality of staple apertures configured to eject staples housed in the cartridge body and a staple retainer removably coupled to the cartridge body. The staple retainer comprises a main body portion configured to at least partially cover the plurality of staple apertures in a position of the staple retainer coupled to the cartridge body, a first handling portion extending from the main body portion at a distal end portion of the staple retainer, and a second handling portion proximal the first handling portion and coupled to the main body portion by a flexure. The second handling portion is elastically deflectable about the flexure and relative to the main body portion of the staple retainer from a neutral, first position to a deflected second position.

In accordance with at least another exemplary embodiment, a method of installing a reload cartridge body in a stapler instrument comprises inserting the reload cartridge body in a jaw of the stapler instrument, the reload cartridge body being coupled to a staple retainer, applying a first force to a first handling portion of the staple retainer to remove the staple retainer, and while applying the first force, applying a second force to a second handling portion of the staple retainer to press the second handling portion against the reload cartridge body toward the jaw of the stapler instrument.

In accordance with yet another exemplary embodiment, a stapler cartridge reload assembly comprises a staple retainer comprising a first side and a second side opposite the first side, a first reload cartridge body removably coupled to the first side of the staple retainer, and a second reload cartridge body removably coupled to the second side of the staple retainer.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and they are incorporated in and constitute a part of this specification. The drawings illustrate one or more exemplary embodiments of the present disclosure and, together with the description, explain certain principles and operation. In the drawings.

DETAILED DESCRIPTION

The present disclosure contemplates various exemplary embodiments of stapler reload cartridges that provide for a relatively small overall size profile, while allowing sufficient space to receive relatively large staples. In some embodiments, stapler reload assemblies including such staple reload cartridges also facilitate a specified sequence for readying the stapler reload assembly for insertion and use in a stapler instrument. For example, in exemplary embodiments of the disclosure, a stapler reload assembly includes various components that assist in keeping the stapler reload assembly, including staples and associated staple pushers held therein, intact prior to insertion and use in a stapler instrument, such as, for example, during transport of the stapler reload assembly. Those various components, however, are intended to be removed prior to insertion of the stapler reload cartridge into a stapler instrument and/or subsequent use of the stapler instrument with the stapler reload cartridge inserted. Allowing various components of a stapler reload assembly to be removed can allow for provision of relatively small dimensions in a use state of the stapler reload cartridge without sacrificing space to accommodate relatively large size staples.

In accordance with exemplary embodiments of the present disclosure, the stapler reload assembly components that are removable prior to insertion and/or use of the stapler reload cartridge include a cover and a staple retainer.

In various embodiments, each of the staple retainer and the cover includes features that interact with one another to ensure the components are removed in an ordered manner for insertion and subsequent use of the stapler reload cartridge. For example, the cover can include features that mechanically interfere with removal of the staple retainer before the cover is removed. A force applied by the user in an attempt to remove the staple retainer prior to removing the cover can result in generation of an interference force between the cover and the staple retainer to prevent removing the retainer. Such features encourage the user to prepare the stapler reload cartridge for installation in the stapler instrument in a manner that prevents damage to the cartridge, such as loss of staples contained in the cartridge or deformation of the cartridge during installation.

Figure 1:
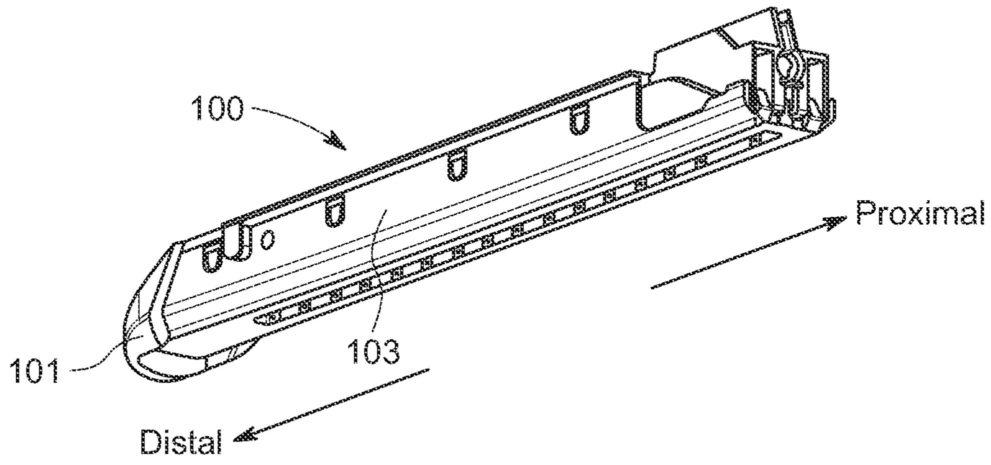
FIG. 1 (Prior Art)
FIG. 1 is a perspective view of an embodiment of a stapler reload assembly according to the prior art.

FIG. 1 shows a prior art stapler reload cartridge 100 for use with an endoscopic surgical stapler instrument. Exemplary surgical stapler instruments that are compatible for use with replaceable stapler reload assemblies are disclosed, for example, by U.S. Pat. Nos. 9,259,275; 8,876,857; 8,852,174; 9,924,941; and 8,991,678; by U.S. Patent Application Publication Nos. US 2013/0105552; US 2019/0053801; and US 2019/0038371; and by International Patent Application Publication Nos. WO 2018/049198; WO 2018/049211; WO 2018/049206; and WO 2018/071497, the entire contents of each being incorporated by reference herein.

Stapler reload cartridge 100 includes a cartridge body 101 that provides a housing to hold a plurality of staples (not shown) to be ejected from the cartridge body 101 in response to actuation of a stapler instrument in which the stapler reload cartridge 100 is inserted. Pushers (not shown) are also contained within the cartridge body 101, and the pushers serve to push the staples from the cartridge during firing of the stapler instrument, as those having ordinary skill in the art are familiar with. Stapler reload cartridge 100 has a cover 103 that is intended to be irremovably installed onto the cartridge body 101 during manufacturing assembly. In the stapler reload cartridge 100, the cover 103 is formed of sheet metal, such as, for example, sheet steel or aluminum alloy. The cover 103 serves to retain the staples and associated pushers housed within the cartridge body 101 and prevent them from inadvertently falling out, e.g., during manufacturing, shipping, or installation of the stapler reload cartridge 100 in a stapler instrument.

Figure 2:
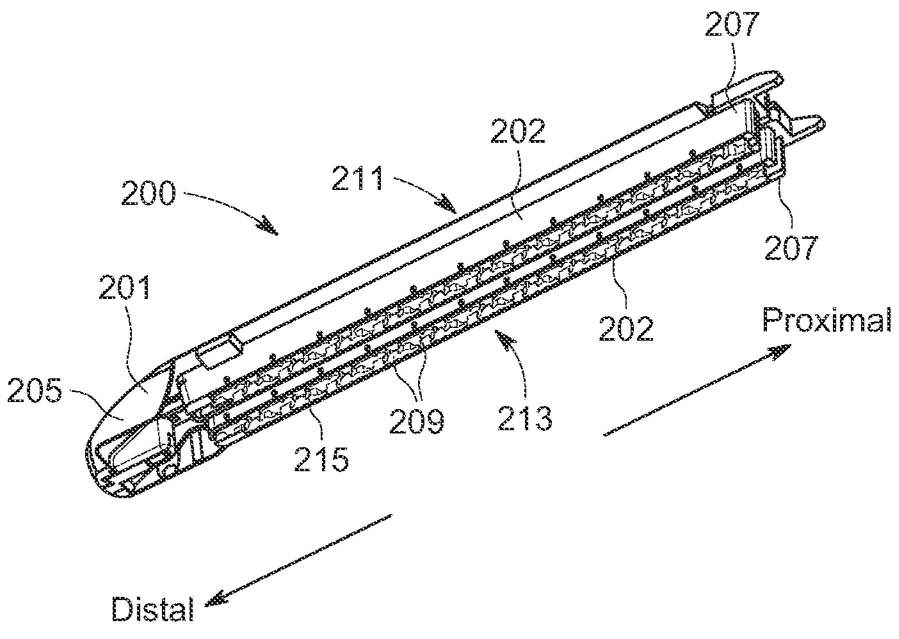
FIG. 2 is a perspective view of an embodiment of a stapler reload cartridge body according to one embodiment of the present disclosure.
Figure 9A:
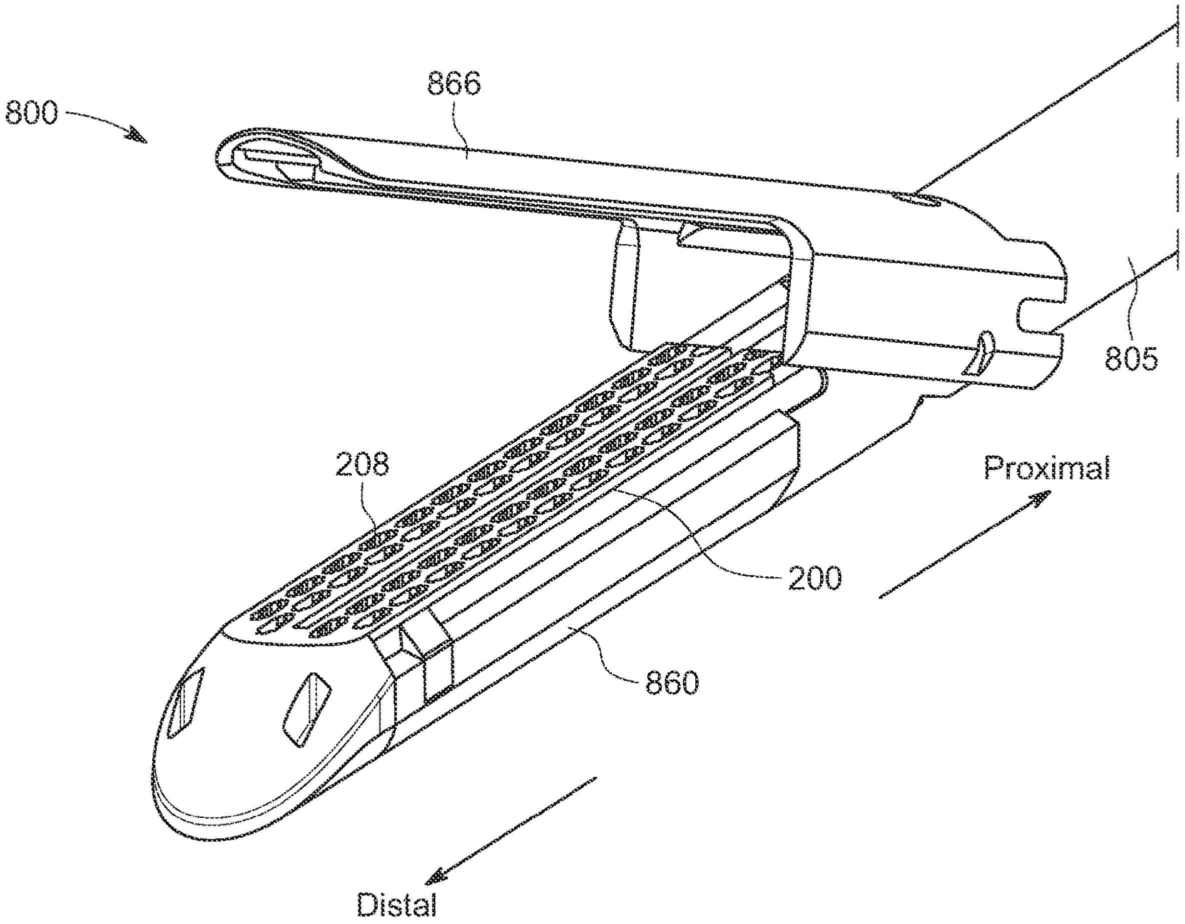
FIG. 9A illustrates a perspective view of the stapler instrument of FIG. 8 with the stapler reload cartridge of FIG. 3A installed in the jaw, with the cover removed and the retainer in place.

Referring now to FIG. 2, an embodiment of a stapler reload cartridge 200 according to an embodiment of the present disclosure is shown. As can be seen in FIG. 2, the stapler reload cartridge 200 includes a cartridge body 201 having a staple ejection side 211 and a pusher loading side 213 opposite the staple ejection side 211. The cartridge body 201 houses a plurality of staples (not shown) that can be ejected from the cartridge body 201 through staple apertures (e.g., staple apertures 208 as best shown in FIG. 9A) in the staple ejection side 211 during use of a stapler instrument in which the cartridge body 201 holding the staples is installed. As an example, and without limitation, staple ejection side 211 of the cartridge body 201 is configured to accept staples during manufacturing of the stapler reload cartridge 200. During use, components of the stapler instrument, such as a sled or other staple firing apparatus as would be familiar to those of ordinary skill in the art, act on the staple pushers through the pusher loading side 213 of the cartridge body 201 and the staples are ejected from the staple ejection side 211 of the cartridge body 201. Unlike the stapler reload cartridge 100 of FIG. 1, the stapler reload cartridge 200 does not have a permanent, irremovable cover corresponding to cover 103 of the stapler reload cartridge 100 of FIG. 1. Because the stapler reload cartridge 200 does not include such a cover, the stapler reload cartridge 200 can accept relatively large sized staples while maintaining a relatively small overall size profile (e.g., cross-sectional dimensions) because the space normally occupied by such a permanent cover is available to accommodate relatively larger staples.

Because stapler reload cartridge 200 does not include a permanent cover, the staples and other internal components of the stapler reload cartridge 200 could potentially fall out of the stapler reload cartridge 200 during manufacturing, shipping, or other transport/handling of the stapler reload cartridge 200.

Further, in some embodiments, the stapler reload cartridge body 201 has a generally U-shaped form in plan view. That is, the legs 202 are connected to one another at a distal end 205 of the cartridge body 201 and extend unsupported to proximal ends 207, generally forming a U-shape. In the prior art embodiment of FIG. 1, the cover 103 also serves to reinforce and hold the legs 202 in position to prevent bending or other deformation of the legs, as well as other potential damage to the reload cartridge body.

Figure 8:
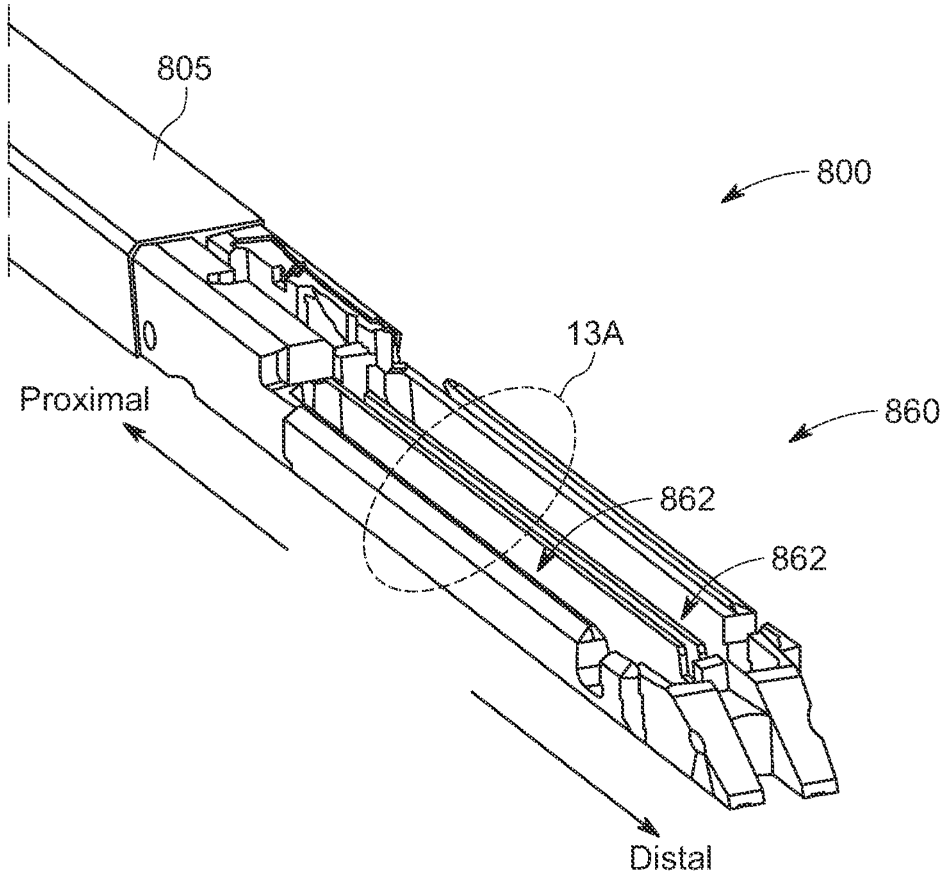
FIG. 8 illustrates a perspective view of a stapler instrument showing a shaft an end effector jaw configured to removably receive a stapler reload assembly according to an embodiment of the disclosure.

The stapler reload cartridge 200 is configured to be accepted into a jaw of a stapler instrument. For example, referring now to FIG. 8, a cartridge-retaining jaw 860 of a stapler instrument 800 according to an embodiment of the present disclosure is shown. The cartridge-retaining jaw 860 can be attached to a shaft 805 (shown in FIGS. 8, 9A, and 9B) that extends proximally to an actuation mechanism. The actuation mechanism can be or include a force transmission mechanism actuated by a teleoperated surgical systems that operate at least in part with computer assistance, such as the da Vinci® Surgical Systems commercialized by Intuitive Surgical, Inc., of Sunnyvale, California. Other systems can include other computer-assisted mechanisms or manually operated actuation mechanisms.

Figure 9B:
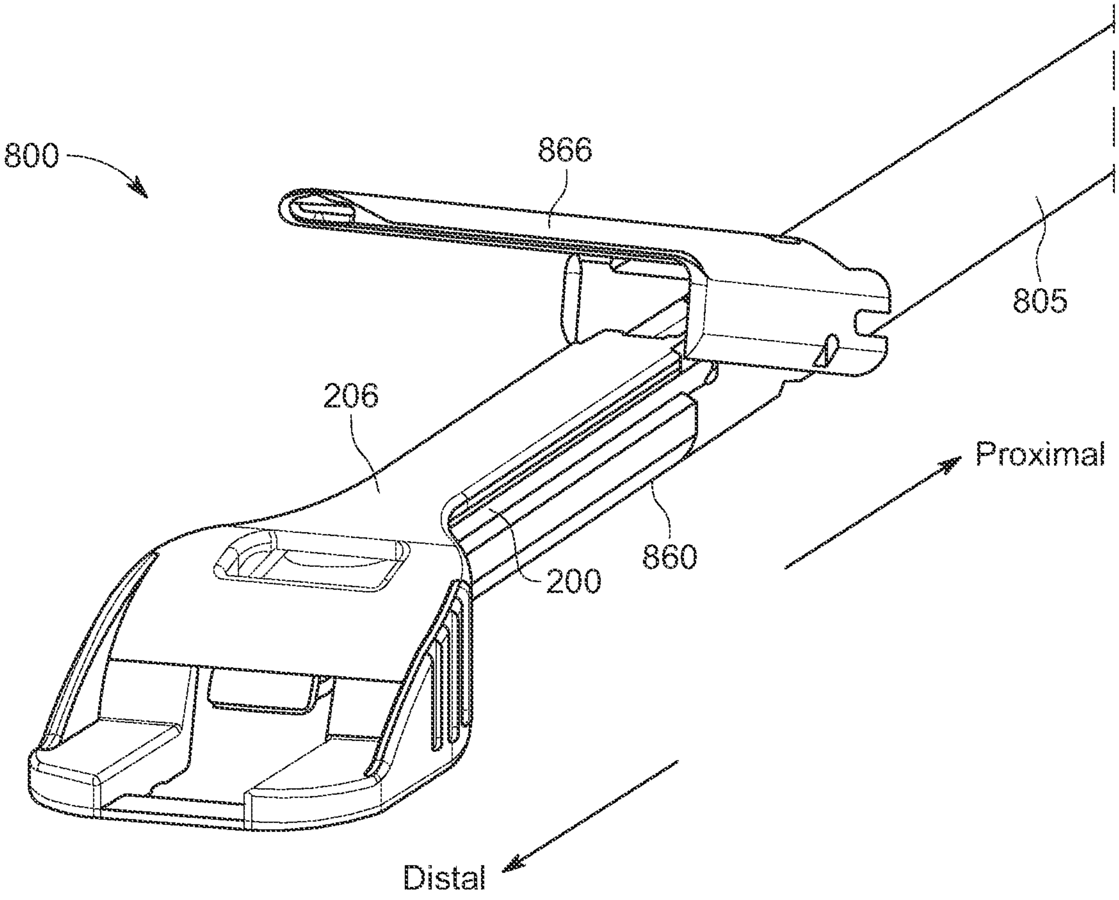
FIG. 9B illustrates a perspective view of the stapler instrument of FIG. 9A with the staple retainer removed from the stapler reload cartridge.

The cartridge-retaining jaw 860 includes longitudinal channels 862 configured to accept legs 202 (FIG. 2) of the cartridge body 201. FIG. 9A shows the stapler reload cartridge 200 installed in the cartridge-retaining jaw 860 of the stapler instrument 800, with an anvil 866 of the stapler instrument 800 also depicted. In the view of FIG. 9B, a staple retainer 206 (which may be of a configuration as is discussed in detail further below in connection with various embodiments, with the retainer configuration of the embodiment of FIGS. 3A-3G being depicted) is in place over the stapler reload cartridge 200 to prevent staples from migrating from the stapler reload cartridge 200 while a user installs the stapler reload cartridge 200 in the cartridge-retaining jaw 860 of the stapler instrument 800. Once the stapler reload cartridge 200 is installed in the stapler instrument 800, the staple retainer 206 is removed by the user and the stapler instrument 800 is ready for use, as shown in FIG. 9A.

As those having ordinary skill in the art are familiar, in use, the stapler instrument 800 can be operated to clamp tissue between the cartridge-retaining jaw 860 and the anvil 866. The clamped tissue is cut with a cutting element (not shown) that advances along the tissue through the cartridge-retaining jaw 860 and the staples are fired by a sled (not shown) that advances through the cartridge-retaining jaw 860 and forces staples out through staple apertures 208 of the stapler reload cartridge 200, through the clamped tissue, and against the anvil 866.

Referring again to FIG. 2, the stapler reload cartridge 200 includes pushers 209 against which the sled or other staple-installing component bears to force the staples from the stapler reload cartridge 200. The sled's action against the pushers 209 forces the staples through the apertures (208 shown in FIG. 9A), through the tissue, and against the anvil 866 (FIGS. 9A and 9B). The pushers 209 are at least partially exposed on the pusher loading side 213 of the stapler reload cartridge 200 through pusher apertures 215, through which the pushers 209 are accessible to components of the stapler instrument (such as a sled) during use. During manufacturing, the pushers 209 are installed in the cartridge body 201 through the pusher apertures 215, after which the cartridge body 201 may be transferred to a different manufacturing station for loading of the staples through staple apertures 208 (see FIG. 9*a*) such that each staple is coupled to a corresponding pusher 209. In the absence of a permanent cover, such as cover 103 in FIG. 1, the pushers 209 could potentially fall out of the cartridge body 201 or migrate to an incorrect position before the staples are loaded. Additionally, once the staples are loaded, the staples could inadvertently advance through the staple apertures 208 during shipping of the stapler reload cartridge 200 or handling of the stapler reload cartridge 200 prior to, or during installation of the stapler reload cartridge 200 in the stapler instrument 800.

To ensure the pushers and staples are retained within a stapler reload cartridge until ready for installation and subsequent use, and to prevent damage of the cartridge body, various embodiments disclosed herein provide stapler reload assemblies that one or more removable components that are kept in place until the stapler reload cartridge is ready for use. In exemplary embodiments of the disclosure, stapler reload assemblies provide the stapler reload cartridge with a staple retainer and a cover, which are in place over the stapler reload cartridge at various times during transport and installation into a stapler instrument. The staple retainer and cover can optionally be designed to encourage an ordered sequence for removal of the cover and retainer, to help ensure that the staples and pushers are retained within the stapler reload cartridge until ready for installation and subsequent use in a stapler instrument. In some embodiments, the staple retainer and cover include various interlocking features that operably engage to dictate an ordered sequence for removal of those components from the stapler reload cartridge.

Additionally or alternatively, a force required to be applied to the staple retainer to remove the staple retainer from the cartridge may be different from a force required to be applied to the cover to remove the cover from the cartridge. Such a configuration can assist in providing an ordered sequence of removal of the cover and staple retainer.

Figure 3A:
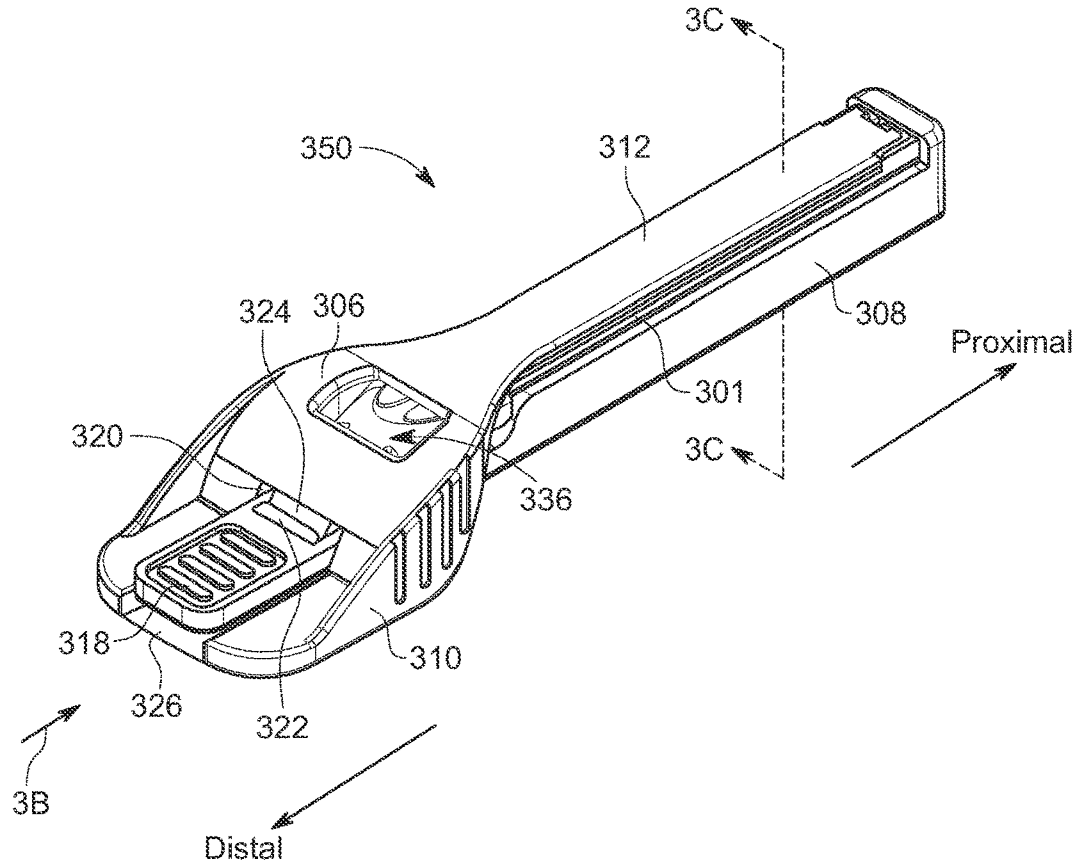
FIG. 3A is a perspective view of a stapler reload assembly in a fully assembled configuration with a cover and retainer in place according to an embodiment of the present disclosure.

Referring now to FIG. 3A, an exemplary embodiment of a stapler reload assembly 350 is shown. Stapler reload assembly 350 includes a staple retainer 306 installed over and covering at least a portion of a staple ejection side of a stapler reload cartridge body 301 (the staple ejection side being similar to 211 of stapler reload cartridge 200 in FIG. 2). The stapler reload assembly 350 also includes a cover 308 installed over and covering at least a portion of a pusher loading side of the stapler reload cartridge body 301 (the pusher loading side being similar to pusher loading side 213 of stapler reload cartridge 200 in FIG. 2). The cover 308 is configured to be installed over the stapler reload cartridge body 301 during manufacturing to hold pushers (similar to pushers 209 described with reference to the embodiment of FIG. 2) in place while the stapler reload cartridge body 301 is moved during manufacturing, for example, to another station for loading the staples. Once the staples are loaded, the staple retainer 306 is installed over the stapler reload cartridge body 301 to ensure the staples do not migrate through staple apertures (reference being made to staple apertures 208 shown in FIG. 9A) prior to installation and use of the stapler reload cartridge body 301. Thus, for purposes of packaging, shipping, and handling, the pushers and staples are fully retained within the stapler reload cartridge body 301 by the cover 308 and staple retainer 306.

The staple retainer 306 and cover 308 each include various complementary mating features to retain each of the staple retainer 306 and cover 308 on a stapler reload cartridge body 301, as well as to couple the staple retainer 306 and the cover 308 together. It is desired that the cover 308 be removed before removing the staple retainer 306, so that the stapler reload cartridge body 301 can be installed within the stapler instrument prior to removing the staple retainer 306, so as to avoid staples migrating out of the stapler reload cartridge body 301 prior to use in the stapler instrument. In the embodiment of FIG. 3A, the staple retainer 306 and cover 308 include complementary engagement features that interlock and provide for the removal of the staple retainer 306 and cover 308 in an ordered sequence.

For example, in the embodiment of FIG. 3A, to install the stapler reload assembly 3550 in a stapler instrument, the cover 308 must first be removed. The stapler reload cartridge body 301, carrying the pushers and staples, can then be installed in a cartridge-retaining jaw of the stapler instrument. The continued presence of the staple retainer 306 during such installation retains the staples within the stapler reload cartridge body 301 and also reduces a risk of bending of the legs 202 (FIG. 2) of the stapler reload cartridge body 301 during insertion into the jaw. Once the stapler reload cartridge body 301 is installed within the stapler instrument, the staple retainer 306 can be removed to ready the stapler instrument for actuation to fire staples.

To promote an ordered sequence for readying and installing the stapler reload cartridge body 301 within the stapler instrument, the staple retainer 306 and cover 308 both include complementary mating features that prevent the staple retainer 306 from being removed when the cover 308 is still in place on the stapler reload cartridge body 301.

Referring still to FIG. 3A, the staple retainer 306 includes a handling portion 310 at a distal end portion thereof (relative proximal and distal directions being labeled) and a top plate 312 that covers the staple ejection side of the stapler reload cartridge body 301. The cover 308 covers the pusher loading side of the stapler reload cartridge body 301.

At the distal end portion of the stapler reload assembly 350, the cover 308 includes a tab member 318 that extends through an aperture 320 in the handling portion 310 of the staple retainer 306. The tab member 318 has a ridge 322 that engages a lip 324 that extends from the staple retainer 306 within the aperture 320. A crossbar 326 extends across the bottom of the handling portion 310 of the staple retainer 306 beneath the tab member 318. It can be seen from the view in FIG. 3B that when an attempt is made to remove the staple retainer 306 from the stapler reload cartridge body 301 (e.g., by attempting to lift the staple retainer 306 up and away from the stapler reload cartridge body 301) while the cover 308 is in place, a mechanical interference force between the tab member 318 and the crossbar 326 occurs to prevent the removal of the staple retainer 306. Further, when an attempt is made to slide the staple retainer 306 in the distal direction and off the stapler reload cartridge body 301, a mechanical interference between the ridge 322 and the lip 324 occurs to prevent such removal.

Figure 3B:
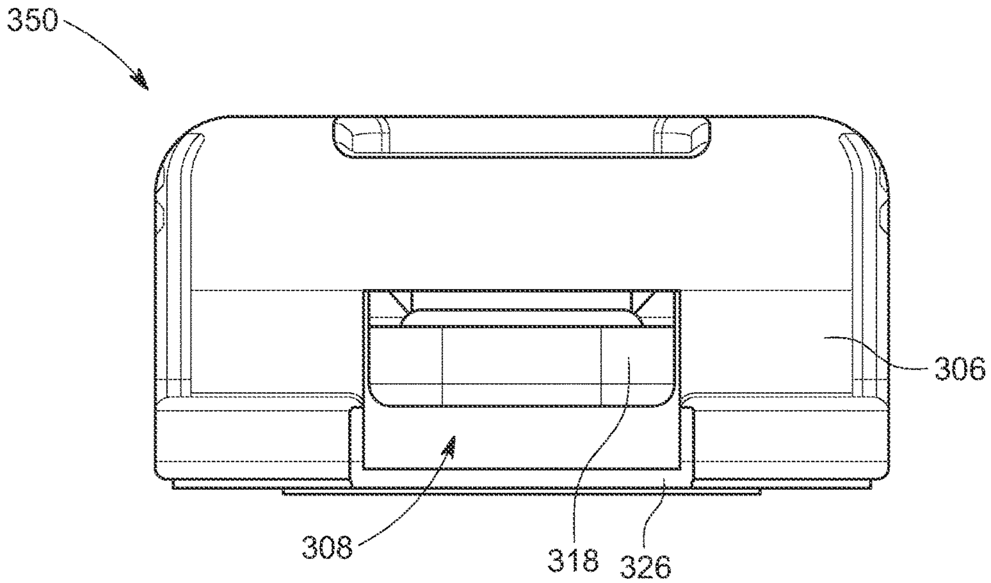
FIG. 3B is an end view of the stapler reload assembly of FIG. 3A taken from direction 3-B shown in FIG. 3A.
Figure 3C:
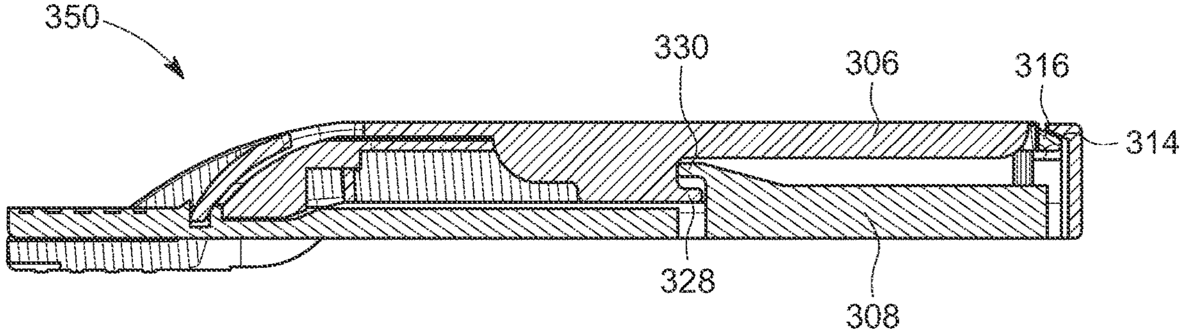
FIG. 3C is a cross-sectional view, taken through section 3-C shown in FIG. 3A, of the stapler reload assembly of FIG. 3A.

Further, as shown in FIG. 3C, which shows a cross-sectional view of the stapler reload assembly 3550 from the perspective 3C-3C in FIG. 3A, the staple retainer 306 and cover 308 each include corresponding, interlocking complementary tongue portions 328 and 330 extending along the proximal-distal directions. Interference force between the complementary tongue portions 328 and 330 also help to prevent the staple retainer 306 from being removed from the stapler reload cartridge body 301 when the cover 308 is in place. At a proximal end portion, the cover 308 includes a recess 314 into which a protrusion 316 of the stapler reload cartridge body 301 is received, providing an engagement to assist in retaining the proximal end portion of the cover 308 on the stapler reload cartridge body 301.

Figure 3D:
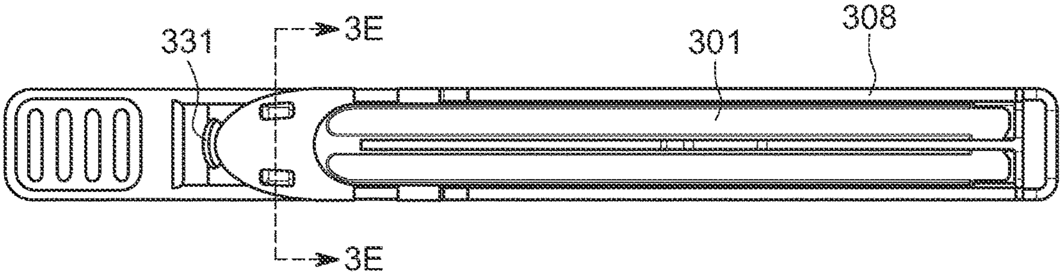
FIG. 3D is a top plan view of the stapler reload cartridge body and cover of FIG. 3A, with the staple retainer of FIGS. 3A-3C removed.
Figure 3E:
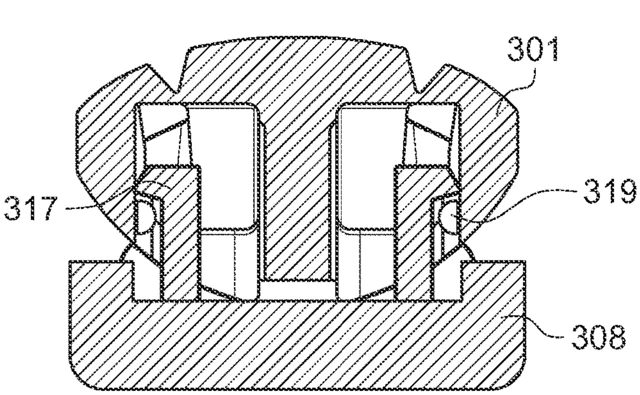
FIG. 3E is another cross-sectional view, taken through section 3-E in FIG. 3A, of the stapler reload assembly of FIG. 3A.

FIG. 3D is a plan view of the staple ejection side illustrating the cover 308 in place on the stapler reload cartridge body 301 while omitting the staple retainer 306 to better illustrate features of the cover 308 that aid in retention of the cover 308 on the stapler reload cartridge body 301. The cover 308 includes a shoulder 331 that, along with the recess 314 (FIG. 3C) into which protrusion 316 (FIG. 3C) is received, limits longitudinal (proximal and distal direction) movement of the stapler reload cartridge body 301 and the cover 308 relative to each other. Referring now to FIG. 3E, a cross-sectional view of the stapler reload cartridge body 301 and cover 308 along cross-section 3-E-3-E labeled in FIG. 3D is shown to illustrate additional retaining features of the cover 308. The cover 308 includes retaining arms 317 that engage with protrusions 319 formed on the interior of the stapler reload cartridge body 301 to retain the cover 308 on the stapler reload cartridge body 301. While the retaining arms 317 are shown specifically in connection with the embodiment of FIGS. 3A-3G, similar features can be used in any of the embodiments of the present disclosure.

Figure 3F:
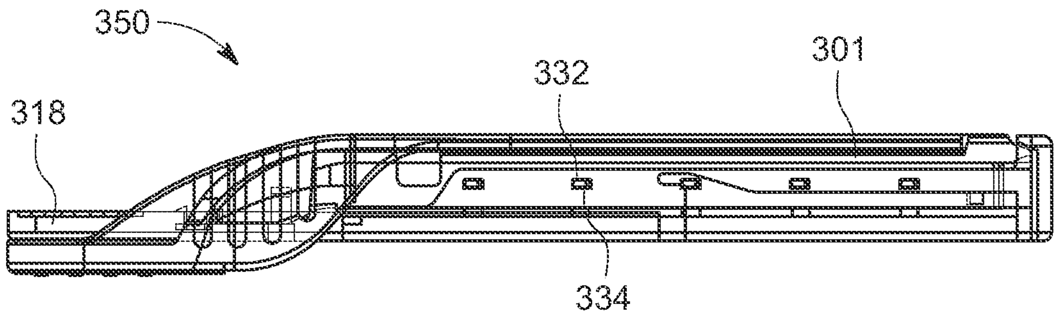
FIG. 3F is a side elevation view of the stapler reload assembly of FIG. 3A.

Referring now to FIG. 3F, a side elevation view of the stapler reload assembly 350 is shown, with portions shown transparent or hidden to reveal features of the stapler reload cartridge body 301. The stapler reload cartridge body 301 includes one or more detents 332 in a side portion of the stapler reload cartridge body 301, into which retention tabs 334 of the staple retainer 306 extend to retain the cover 308 on the stapler reload cartridge body 301. To remove the cover 308, a downward force can be applied to the tab member 318 (the force being applied to move the tab member 318 away from the cartridge body 301). The tab member 318 of the cover 308 deflects downward (by virtue of the space between the tab 318 and the crossbar 326, as can be seen in FIG. 3B) and allows the ridge 322 to disengage from the lip 324 (FIG. 3A). Once this disengagement occurs, a force can be applied to move the cover in the proximal direction, causing the retention tabs 334 of the cover 308 to disengage the detents 332 of the stapler reload cartridge body 301. In some embodiments, the retention tabs 334 can optionally comprise ramps on the proximal-facing side to facilitate removal of the staple retainer 306 when a proximally-directed force is applied and the tab member 318 is depressed.

Figure 3G:
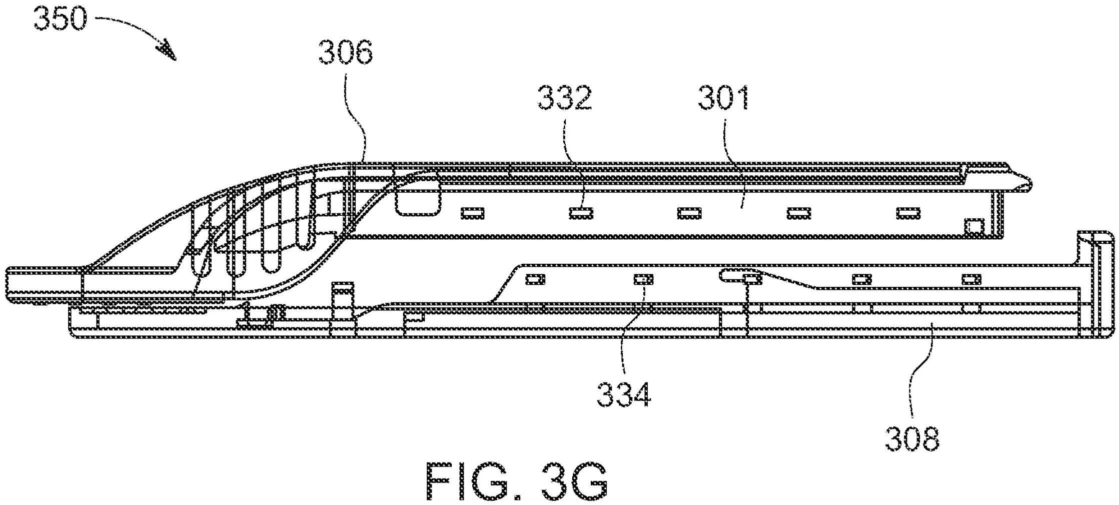
FIG. 3G is a side elevation view of the stapler reload assembly of FIG. 3A in a partially assembled configuration with the cover partially removed.

As shown in FIG. 3G, once the cover 308 has been moved sufficiently in the proximal direction such that the tab member 318 of the cover 308 clears the crossbar 326 of the staple retainer 306 and the complementary tongue portions 328 and 330 (FIG. 3C) disengage, the cover 308 can be moved downwardly and away from the stapler reload cartridge body such that it can be completely removed from the stapler reload cartridge body 301, leaving the staple retainer 306 in place on the stapler reload cartridge body 301. In this configuration, the stapler reload cartridge body 301 is ready for installation in a stapler instrument (reference is made to FIG. 9B), after which the staple retainer 306 can be removed from the stapler reload cartridge body 301 and the stapler instrument is ready for use to fire staples from the stapler reload cartridge body 301.

As shown in FIG. 3A, the handling portion 310 includes a window 336 through which a portion of the stapler reload cartridge body 301 can be viewed. The size of staple loaded in the stapler reload cartridge body 301 can optionally be indicated by a color of the stapler reload cartridge body 301, thereby facilitating the user determining the size of staples in the stapler reload assembly prior to installing the stapler reload cartridge body in the stapler. Other indicia, such as a number, can be provided on the stapler retainer or elsewhere to assist in identifying the size of staples carried by the stapler reload assemblies disclosed herein.

The tab member 318 of the cover 308 and the handling portion 310 of the staple retainer 306 can include knurling, ridges, or other surface relief profiles and/or textures on portions of those components that will be handled by the user to facilitate grasping by the user and provide further indication to the user of how to handle and use the stapler reload assembly 350. The staple retainer 306 and cover 308 can be made from any suitable materials such as metal alloys, composite materials, and polymer materials. Suitable materials can include those that exhibit sufficient flexibility to enable function of the various engagement features and retaining features described herein, such as snap fits, friction fits, interference fits, etc. In various exemplary embodiments, the staple retainer 306 and cover 308 are made from polymer materials and can be manufactured by, e.g., injection molding.

Figure 4A:
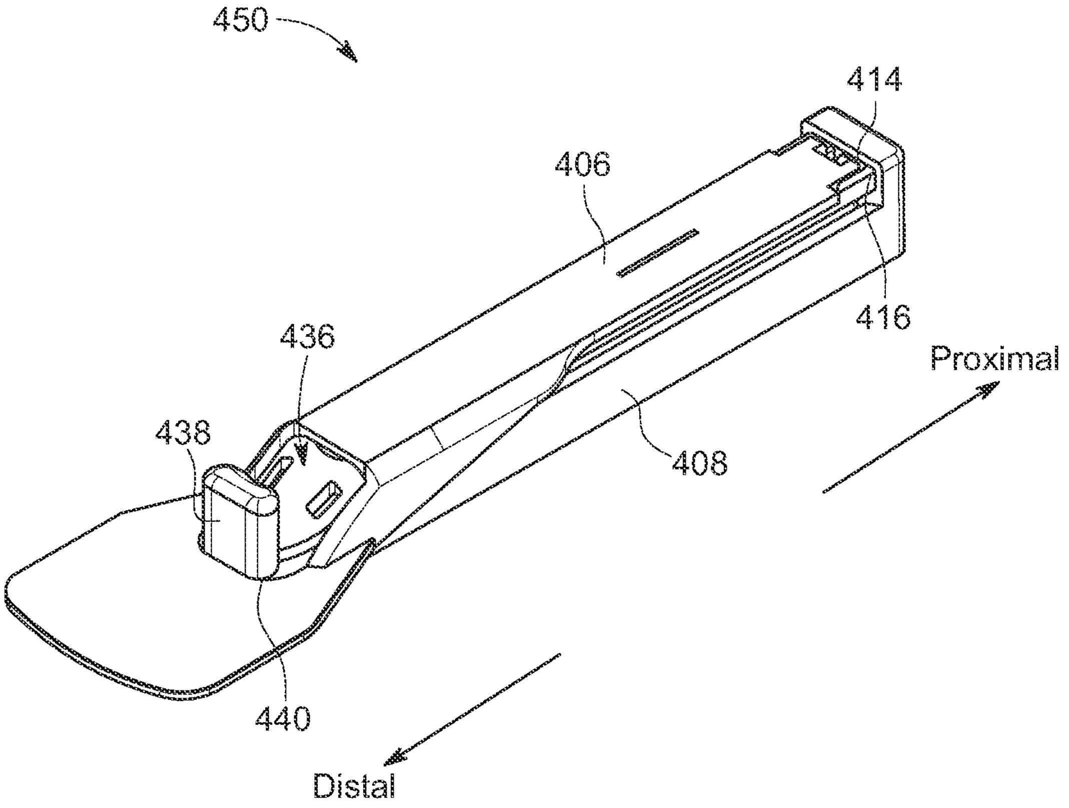
FIG. 4A is a perspective view of another embodiment of a stapler reload assembly in a fully assembled configuration with a cover and retainer in place according to the present disclosure.
Figure 4B:
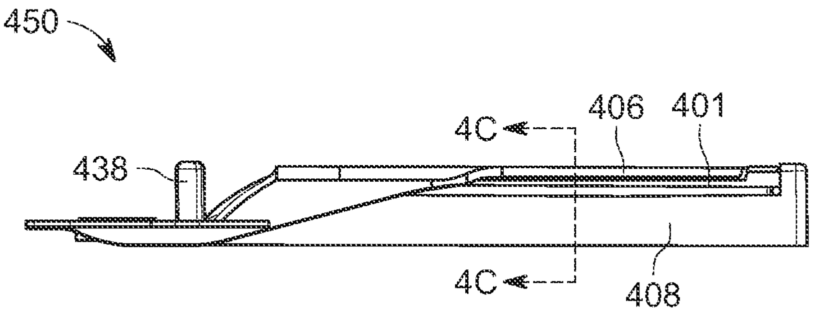
FIG. 4B is a side elevation view of the stapler reload assembly of FIG. 4A.

Referring now to FIGS. 4A and 4B, another embodiment of a stapler reload assembly 450 according to the present disclosure is shown. The stapler reload assembly 450 includes a staple retainer 406 and a cover 408 installed on a stapler reload cartridge body 401, in a generally similar arrangement to the embodiment of FIGS. 3A-3G described above, with various differences being described below. The cover 408 does not include a tab as in the embodiment of cover 308, but instead includes a push tab 438 that extends through an aperture 440 in the staple retainer 406. As with the embodiment of FIGS. 3A-3E, the cover 408 includes a recess 414 that accepts a projection 416 of the stapler reload cartridge body 401. The staple retainer 406 includes a window 436 to enable a user to determine the color and/or other identifying characteristics of the stapler reload cartridge body 401, and by association, the size of staples in the stapler reload cartridge body 401.

Figure 4C:
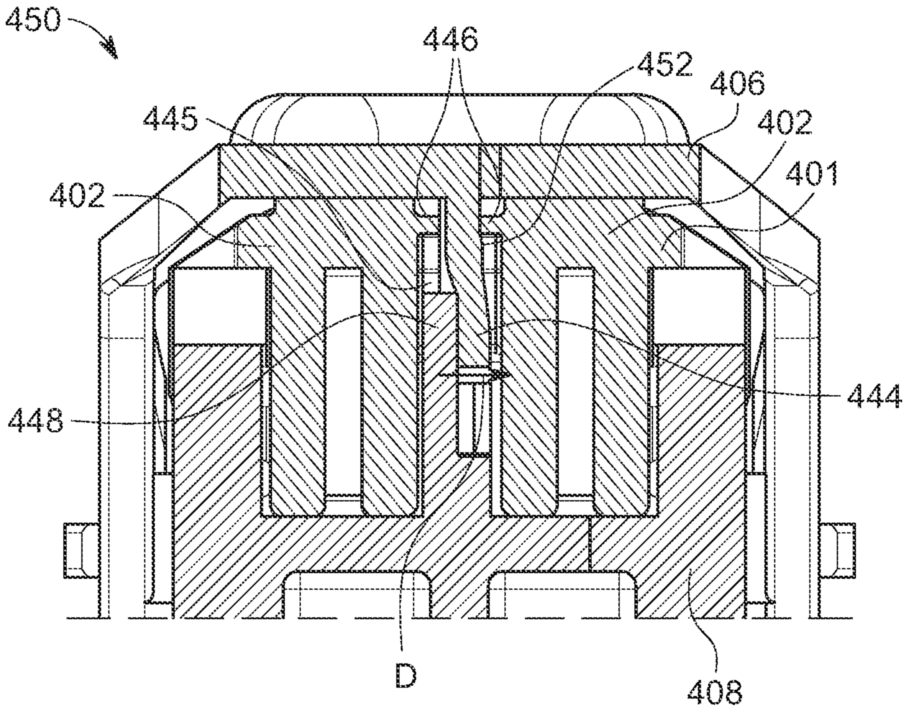
FIG. 4C is a cross-sectional view, taken through section 4-C in FIG. 4A, of the stapler reload assembly of FIG. 4A.

Referring now to FIG. 4C, a cross-sectional view of the stapler reload assembly 450 through section 4-C labeled in FIG. 4B is shown. The view of FIG. 4C shows additional retaining features of the staple retainer 406 and cover 408. The staple retainer 406 includes a septum 444 protruding downward (in the view of FIG. 4C) through a central recess 445 defined between legs 402 of the stapler reload cartridge body 401 between inner flange portions 446. A fin portion 448 on the cover 408 deflects the septum 444 in a lateral direction D, causing a lip 452 on the septum 444 to engage the inner flange portions 446. In this configuration, interference between the lip 452 and the inner flange portions 446 prevents the staple retainer 406 from being removed while the cover 408 is in place on the cartridge body 401.

Figure 4D:
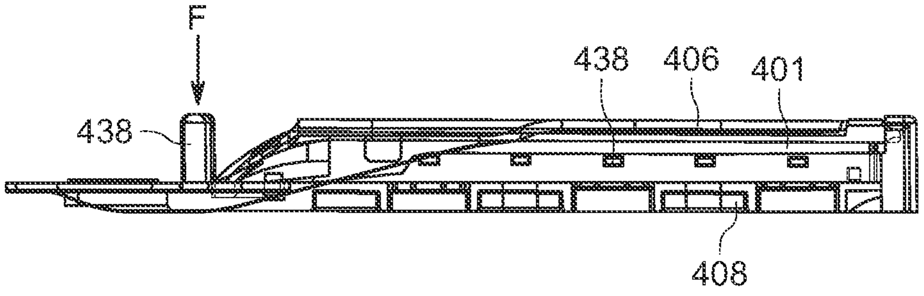
FIG. 4D is a side elevation view of the stapler reload assembly of FIG. 4A.
Figure 4E:
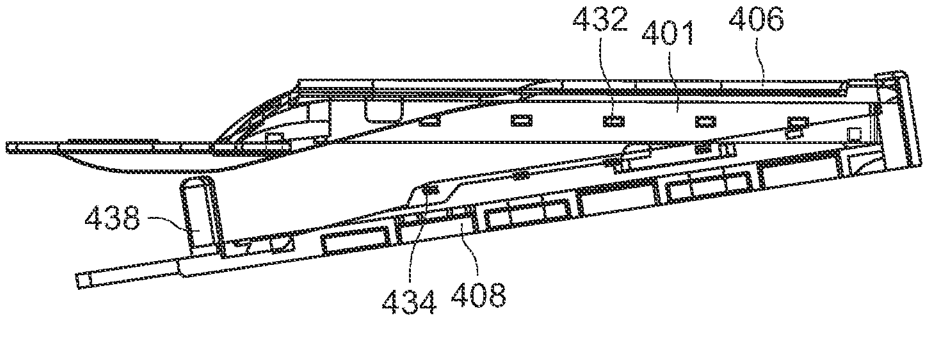
FIG. 4E is a side elevation view of the stapler reload assembly of FIG. 4A in a partially assembled configuration with the cover partially removed.

To remove the cover 408 from the cartridge body 401, a downward force F is applied to the push tab 438, as shown in FIG. 4D. The cover 408 disengages from the cartridge body 401 and generally pivots at a proximal location, as shown in FIG. 4E. Similar to the description above with reference to the embodiment of FIGS. 3A-3G, the cover 408 includes retention tabs 434 that engage detents 432 when the cover 408 is in an installed position (see FIG. 4D). The retention tabs 434 of the cover 408 can have a ramped lower surface to facilitate disengaging from the detents 432 when force F is applied to the push tab 438.

Once the cover 408 disengages and drops away from the cartridge body 401 as shown in FIG. 4E, the fin portion 448 (FIG. 4C) disengages the septum 444 (FIG. 4C) of the staple retainer 406 and allows the septum 444 to return to an undeflected position. The lip 452 (FIG. 4C) disengages the inner flange portion 446 (FIG. 4C), and the staple retainer 406 can be removed from the cartridge body 401, for example after the stapler reload cartridge body 401 is inserted within the stapler instrument.

Figure 5A:
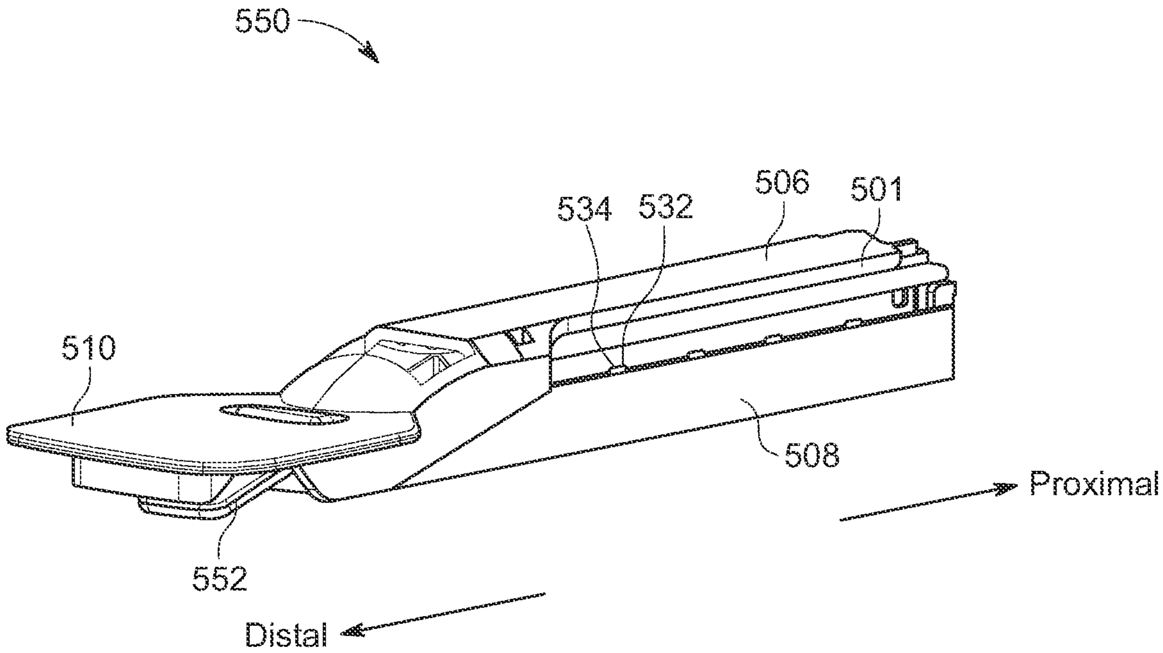
FIG. 5A is a perspective view of a stapler reload assembly in a fully assembled configuration with a cover and retainer in place according to another embodiment of the present disclosure.

Referring now to FIG. 5A, another embodiment of a stapler reload assembly 550 is shown. In the embodiment of FIG. 5A, the stapler reload assembly 550 includes a staple retainer 506 and a cover 508 having a generally similar arrangement with respect to the stapler reload cartridge body 501 as those described above with reference to the embodiments of FIGS. 3 and 4. As with stapler reload assemblies 350 and 450, the cover 508 includes retention tabs 534 that engage detents 532 in stapler reload cartridge body 501 to retain the cover 508 on the stapler reload cartridge body 501.

Figure 5B:
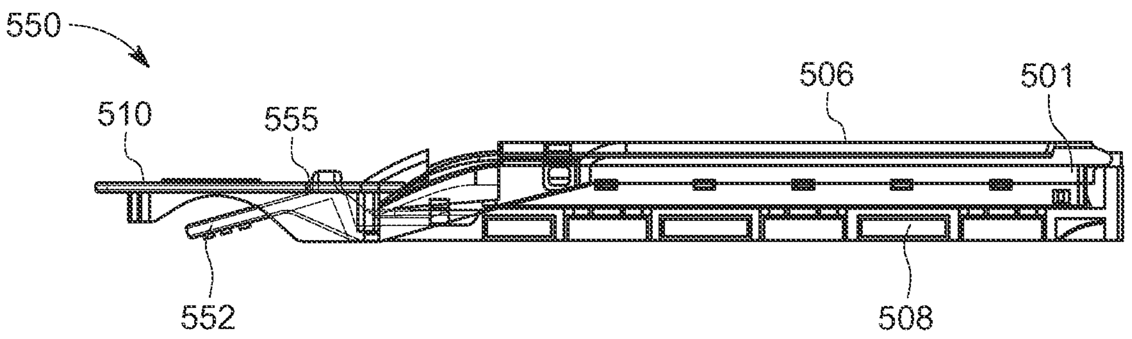
FIG. 5B is a side elevation view of the stapler reload assembly of FIG. 5A.

The staple retainer 506 includes a handling portion 510 at a distal end portion. The cover 508 includes a removal lever 552 positioned underneath the handling portion 510, as shown best in the views of FIGS. 5A and 5B. To remove the cover 508 from the stapler reload cartridge body 501, the handling portion 510 and removal lever 552 are pinched together, which in turn causes the cover 508 to pivot against the staple retainer 506 at fulcrum 555. With reference to FIG. C, the force applied to the removal lever 552 by pinching it upward toward the handling portion 510 causes the cover 508 to be moved in a downward direction away from the stapler reload cartridge body 501, thereby disengaging the retention tabs 534 from the detents 532 of the stapler reload cartridge body 501 and allowing the cover 508 to fully disengage and be removed from the stapler reload cartridge body 501. In the embodiment of FIG. 5A, the handling portion 510 and the removal lever 552 together can be considered as opposing levers.

One or both of the staple retainer 506 and the cover 508 can optionally include features configured to enable the cover 508 and staple retainer 506 to remain coupled together as they are sequentially disengaged from the stapler reload cartridge body 501. Such a configuration could potentially be desirable from a workflow perspective, such as during procedures in which each component of a device must be accounted for. Maintaining the staple retainer 506 and cover 508 as a single assembly throughout the workflow can facilitate use and tracking of the components.

Figure 5C:
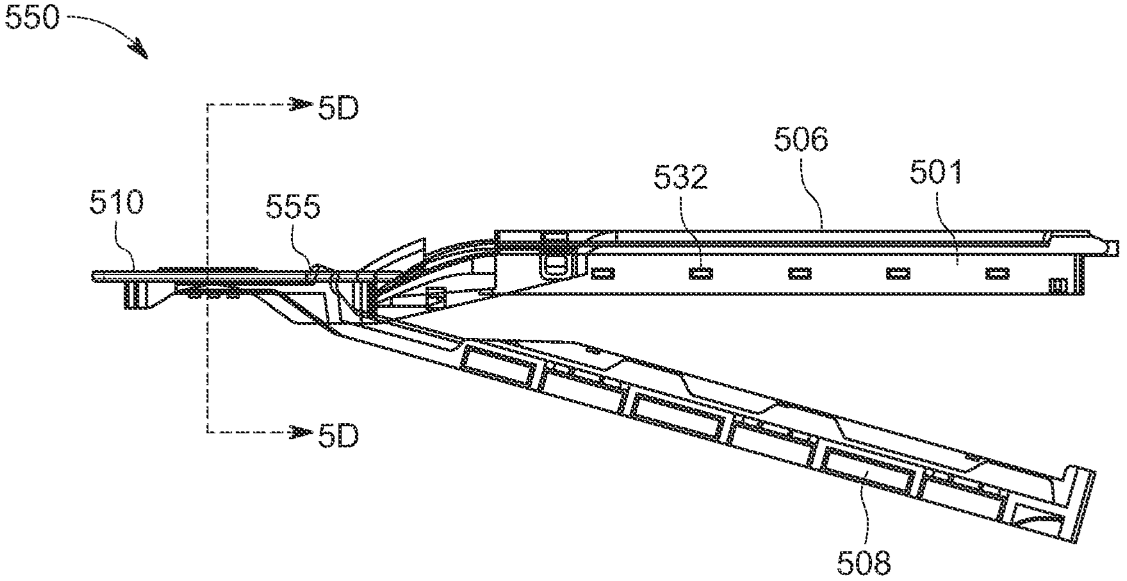
FIG. 5C is a side elevation view of the stapler reload assembly of FIG. 5A in a partially assembled configuration with the cover partially removed.
Figure 5D:
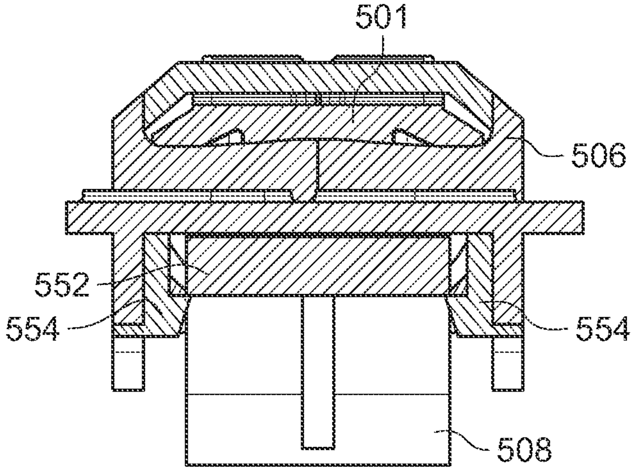
FIG. 5D is a cross-sectional view of the stapler reload assembly of FIG. 5A.

For example, as shown in the embodiment of FIG. 5D, the staple retainer 506 includes two engagement features 554 on either side of the removal lever 552. When the removal lever 552 is depressed and the cover 508 is removed from the stapler reload cartridge body 501, the engagement features 554 engage the removal lever 552 and hold the cover 508 with the staple retainer 506 in the configuration shown in FIG. 5C. Once the cover 508 is removed from the stapler reload cartridge body 501 yet still engaged with the staple retainer 506, as in the configuration of FIG. 5C, the stapler reload cartridge body 501 can be inserted within a stapler instrument. In this configuration, the staple retainer 506 is still engaged with the stapler reload cartridge body 501, and the position of the cover 508 provides clearance for the stapler reload cartridge to be installed in the stapler instrument. The staple retainer 506 and cover 508 can be removed as an assembly (i.e., in the configuration of FIG. 5C) from the stapler reload cartridge body 501 to prepare the stapler instrument for use.

Figure 6:
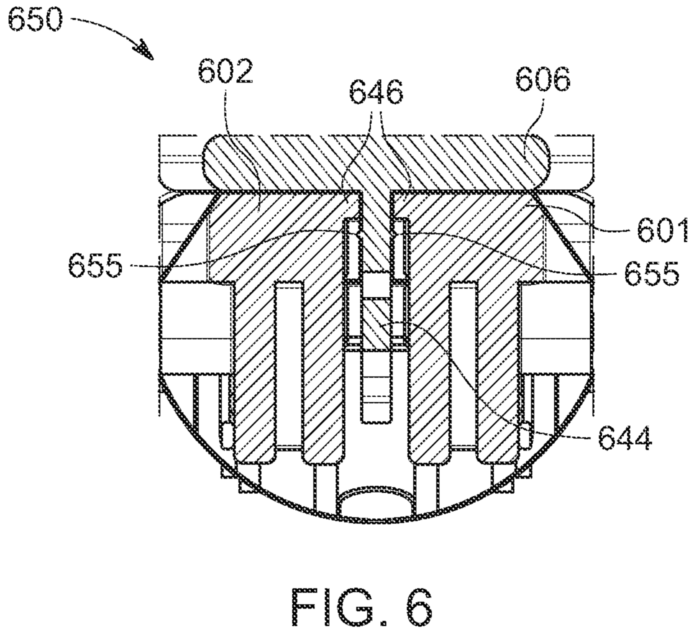
FIG. 6 is a cross-sectional view of a stapler reload assembly according to another embodiment of the present disclosure.
Figure 7:
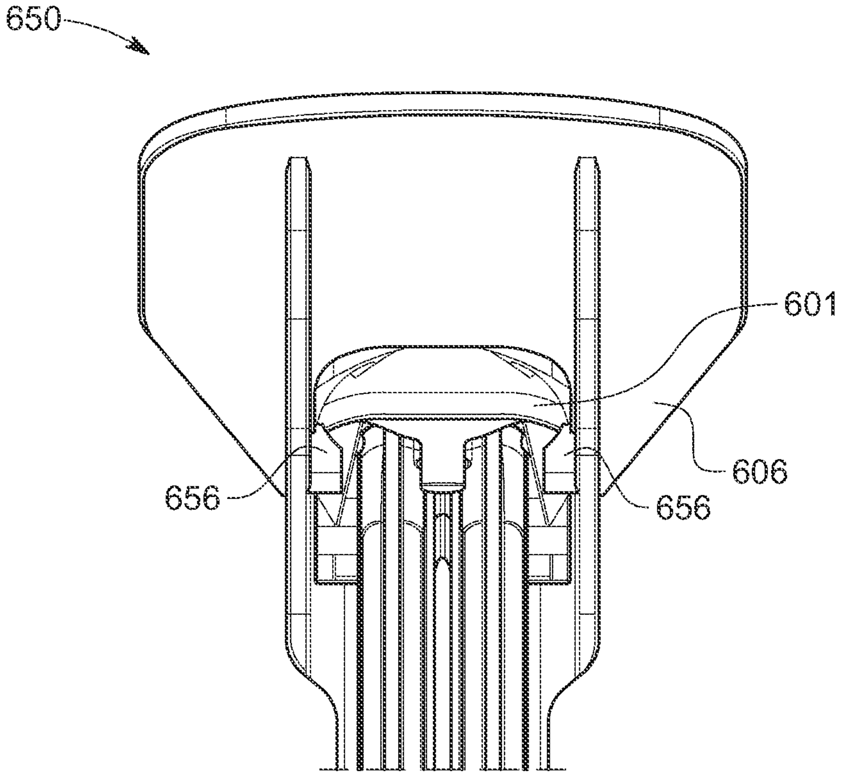
FIG. 7 is a cross-sectional view of the stapler reload assembly according to yet another embodiment of the present disclosure.

FIGS. 6 and 7 illustrate additional retaining features, each of which can optionally be included without limitation on any of the exemplary embodiments of stapler cartridge assemblies described herein. Referring now to FIG. 6, a stapler reload assembly 650 including a stapler reload cartridge body 601 with a staple retainer 606 installed is shown.

For clarity, no cover is shown in FIG. 6. The staple retainer 606 includes a septum 644 that protrudes between inner flanges 646 of the legs 602 of the stapler reload cartridge body 601. As discussed above with reference to the description of FIG. 4C, the septum 644 can prevent undesired deflection of the stapler reload cartridge body legs 602 before the stapler reload cartridge body 601 is installed within the stapler instrument. The septum 644 can also include features configured to ensure the staple retainer 606 is not inadvertently removed prior to installation of the stapler reload cartridge body 601 within the stapler instrument. In the embodiment of FIG. 6, the septum 644 includes ridges 655 that create an interference fit between the inner flanges 646 and the septum 644, thereby inhibiting and discouraging removal of the staple retainer 606 until the stapler reload cartridge body 601 is installed within the stapler instrument.

Referring now to FIG. 7, the staple retainer 606 can include features in addition to those already described above to assist in retaining the staple retainer 606 on the stapler reload cartridge body 601 while the stapler reload cartridge body 601 is inserted within a stapler instrument. For example, as shown in FIG. 7, the staple retainer 606 can include snap fit features 656 that engage the stapler reload cartridge body 601 and maintain the stapler reload cartridge body 601 within the staple retainer 606 while the stapler reload cartridge body 601 is installed within the stapler instrument. For example, the snap fit features 656 can be configured to engage a side of the stapler reload cartridge body 601 opposite a side the staple retainer covers. For example, in the embodiment of FIG. 7, the snap fit features 656 engage a side of the stapler reload cartridge body 601 corresponding to the pusher loading side 213 of cartridge body 201 (FIG. 2). The features shown in the embodiment of FIGS. 6 and 7 can be included, without limitation, on any of the previously described embodiments, such as stapler reload assemblies 350, 450, and 550.

Figure 10A:
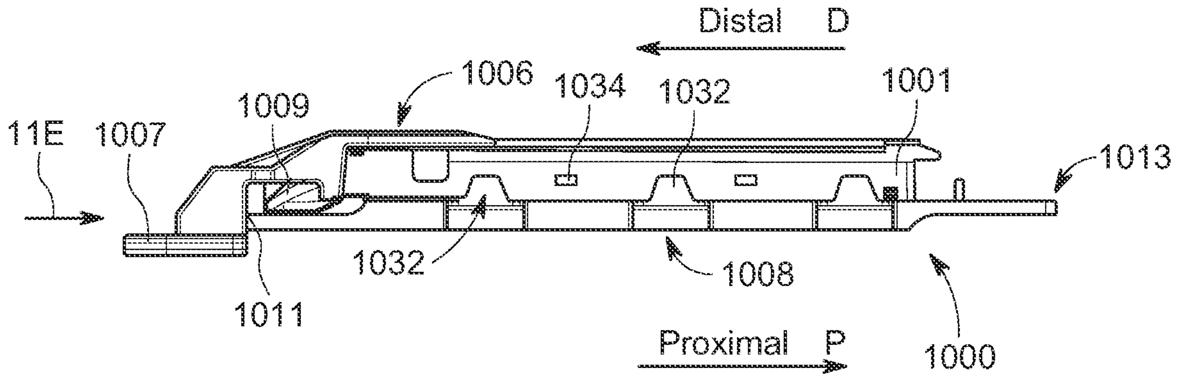
FIG. 10A is a side elevation view of a stapler reload assembly in a fully assembled configuration with a cover and retainer in place according to yet another exemplary embodiment of the present disclosure.
Figure 10B:
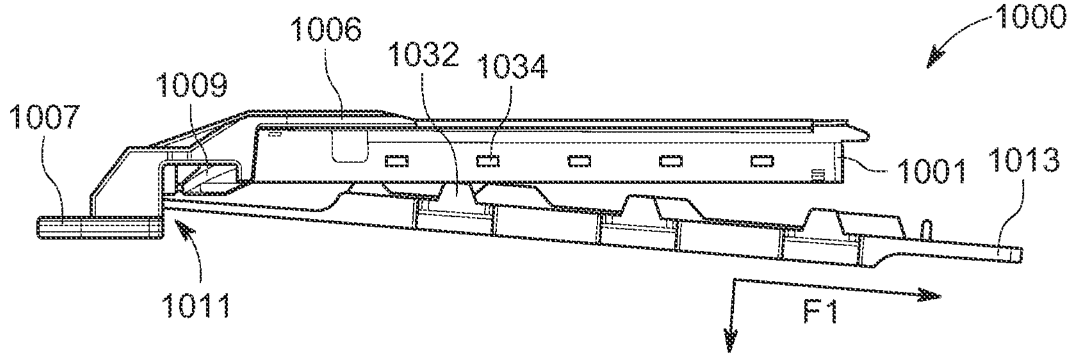
FIG. 10B is a side elevation view of the stapler reload assembly of FIG. 10A in a partly assembled configuration with the cover partially removed.
Figure 10C:
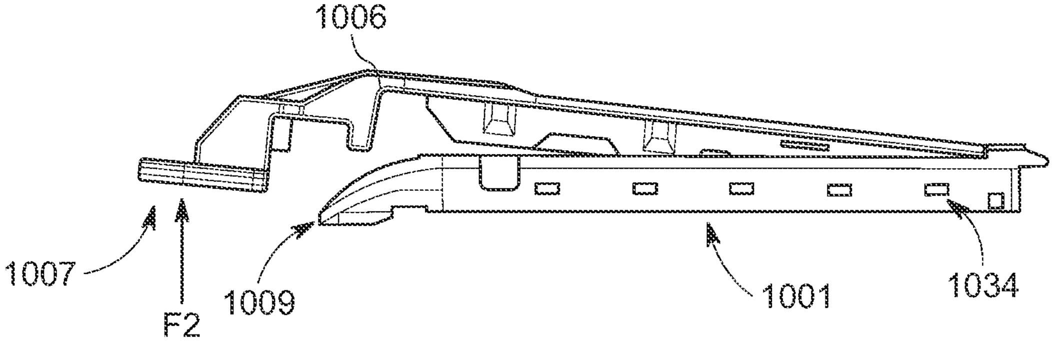
FIG. 10C is a side elevation view of the stapler reload assembly of FIG. 10A in a partly assembled configuration with the cover removed and the retainer partially removed.
Figure 10D:
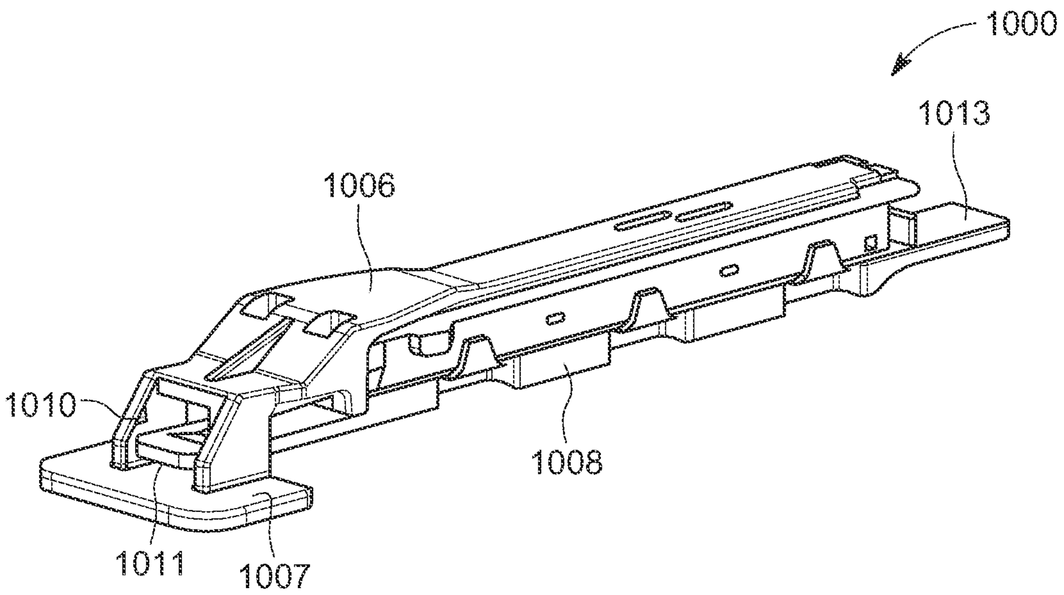
FIG. 10D is a perspective view of the stapler reload assembly of FIG. 10A in a fully assembled configuration.

Referring now to FIGS. 10A-10D, another exemplary embodiment of a stapler reload assembly is shown. The stapler reload assembly 1000 includes a cartridge body 1001, a staple retainer 1006, and a cover 1008. The staple retainer 1006 is removably secured to the cartridge body 1001 by one or more snap features (not shown) and/or friction fit interfaces. The cover 1008 is removably secured to the cartridge body 1001 via engagement of a plurality of retention tabs 1032 that positively engage with corresponding detents 1034 located on an outer surface of the cartridge body 1001. Moreover, the staple retainer 1006 and cover 1008 are operably engaged toward a distal end portion of each of the staple retainer 1006 and cover 1008. When the stapler reload assembly 1000 is fully assembled, a projection 1011 of the cover 1008 extends past a distal tip 1009 of the cartridge body 1001, and through an opening 1010 (FIG. 10D) of the staple retainer 1006. As best shown in FIG. 10D, when both the cover 1008 and the staple retainer 1006 are engaged with the cartridge body 1001, the projection 1011 of the cover 1008 extends through the opening 1010 of the staple retainer 1002 and is positioned atop at least a portion of a tab member 1007 of the staple retainer 1002.

To prepare the stapler reload assembly 1000 for use, the cover 1008 is first removed from the cartridge body 1001. A user can then position the cartridge body 1001 together with the staple retainer 1006 in a cartridge-retaining jaw of a surgical stapler (e.g., cartridge-retaining jaw 860 shown in FIG. 8).

The design of the stapler reload assembly 1000 encourages a user to remove the cover 1008 from the cartridge body 1001 before removing the staple retainer 1006 from the cartridge body 1001. As explained below, interface features between the distal end of the staple retainer 1006 and the distal end of the cover 1008 provides mechanical interference that generally prevents a user from trying to remove the staple retainer 1006 from the cartridge body 1001 prior to removal of the cover 1008.

FIG. 10B shows the stapler reload assembly 1000 in a partly disassembled configuration in which the cover 1008 is being removed from the assembly of the cartridge body 1001 and the staple retainer 1006. Removal of the cover 1008 is accomplished by applying a force F1 to the cover pull tab member 1013 in a proximal and downward direction. Doing so will disengage retention tabs 1032 from the detents 1034 of the cartridge body 1001 and slide the cover 1008 in a proximal direction relative to the assembly of the staple retainer 1006 and cartridge body 1001, disengaging the projection 1011 of cover 1008 from the opening 1010 of the staple retainer 1006. Once the projection 1011 of the cover 1008 is removed from the opening 1010 of the staple retainer 1006, the staple retainer 1006 can be removed completely from the cartridge body 1001.

FIG. 10C shows the assembly of staple retainer 1006 and stapler reload cartridge body 1001, with the cover 1008 removed. In this partly assembled configuration of the stapler retainer reload assembly, staple retainer 1006 can be removed from the stapler reload cartridge body 1001 by applying an upward force F2 on the staple retainer pull tab 1007. Doing so will disengage one or more snap fit features (not shown) and/or friction fit interfaces (not shown) that removably secure the staple retainer 1006 to the cartridge body 1001.

FIG. 10D shows an isometric view of the stapler reload assembly 1000 in a fully assembled configuration (same configuration as FIG. 10A). The projection 1011 of the cover 1008 extends through the opening 1010 of the staple retainer 1006. The projection 1011 is positioned atop pull tab 1007 of the staple retainer 1006. In a manner similar to that described with reference to the embodiment of FIG. 3, this mechanical interface hinders removal of the staple retainer 1006 from the cartridge body 1001 before removal of the cover 1008 from the cartridge body 1001. If a user attempts to remove the staple retainer 1006 by applying an upward force on pull tab 1007 of the staple retainer 1006 (i.e., force F2 shown at FIG. 10C), the projection 1011 of the cover 1008, which is positioned over pull tab 1007 of the staple retainer 1006, will prevent the staple retainer 1006 from being removed from the cartridge body 1001. That is, with the stapler reload assembly 1000 in its fully assembled configuration, the cover 1008 is secured to the cartridge body 1001 and the projection 1011 extends through the opening 1010 of the staple retainer 1006 to prevent the staple retainer 1006 from being removed from the cartridge body 1001.

FIGS. 11A-11E show yet another embodiment of a stapler reload assembly 1100. Stapler reload assembly 1100 includes cartridge body 1101, staple retainer 1106, and cover 1108. The staple retainer 1106 is removably secured to the cartridge body 1101 through one or more snap features (not shown) and/or friction fit interfaces (not shown). The cover 1108 is removably secured to the cartridge body 1101 via engagement of a plurality of retention tabs 1132 that positively engage with corresponding detents 1134 located on an outer surface of the cartridge body.

Stapler reload assembly 1100 is designed to encourage an ordered sequence of removal of the cover 1108 from the cartridge body 1101 before removing staple retainer 1106 from cartridge body 1101. To accomplish this, stapler reload assembly 1100 also employs certain interface features located at a distal end portion of staple retainer 1106 and cover 1108. Cover 1108 includes a T-shaped projection 1113 that extends from an upper surface of the cover 1108. The T-shaped projection 1113 includes transverse portions 1114, best seen in FIG. 11E. The staple retainer 1106 includes inwardly extending lateral projections 1115, also best seen in FIG. 11E. When the stapler reload assembly 1100 is in its fully assembled state, the transverse portions 1114 of the T-shaped projection 1113 and the inwardly extending lateral projections 1115 are arranged such that they will abut each other, with the transverse portions 1114 of the T-shaped projection acting as a stop surface, if a force is applied to the staple retainer 1106 to attempt to remove it from off the stapler reload cartridge body 1101 before the cover 1108 is removed.

Figure 11A:
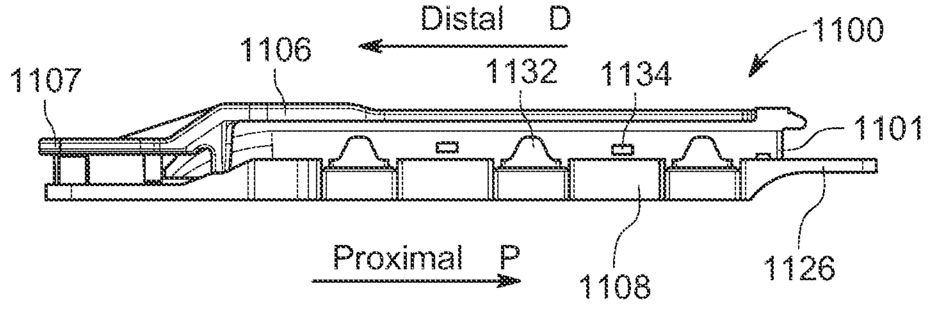
FIG. 11A is a side elevation view of a stapler reload assembly in a fully assembled configuration according to an exemplary embodiment of the present disclosure.
Figure 11B:
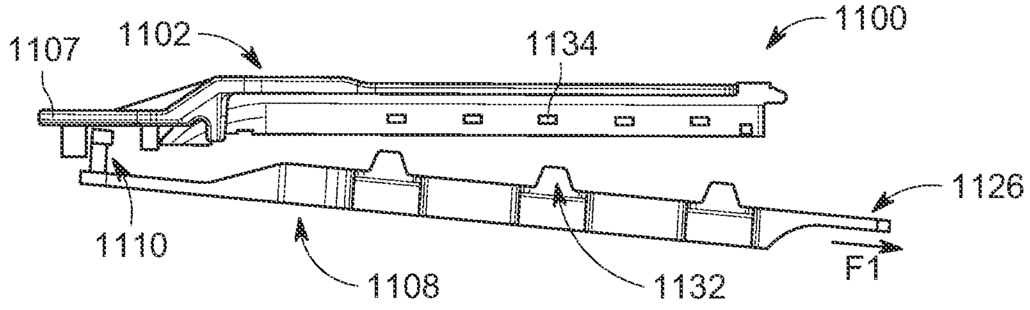
FIG. 11B is a side elevation view of the stapler reload assembly of FIG. 11A in a partly assembled configuration with the cover partially removed.
Figure 11C:
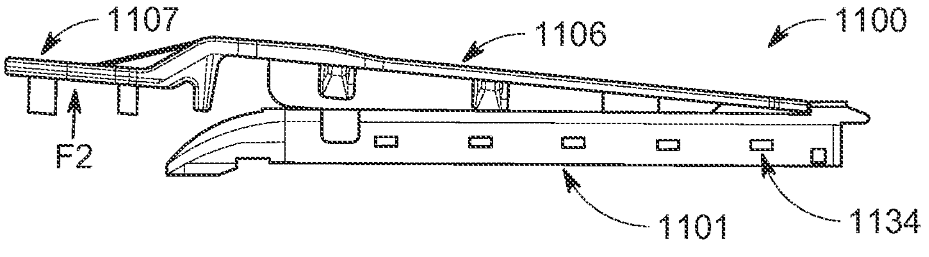
FIG. 11C is a side elevation view of the stapler reload assembly of FIG. 11A in a partly assembled configuration with the cover removed and the retainer partially removed.

FIGS. 11A-11C show an exemplary workflow for preparing the stapler reload assembly 1100 for use. FIG. 11A shows stapler reload assembly 1100 in a fully assembled configuration. FIG. 11B shows the stapler reload assembly 1100 in a partly disassembled configuration with the cover 1108 being removed from the stapler reload cartridge body 1101 and from the staple retainer 1106. Removal of the cover 1108 is accomplished by applying force F1 to pull tab 1126 so as to pull on pull tab 1126 in a proximal P and downward direction. Doing so will disengage retention tabs 1132 of the cover 1108 from the detents 1134 of the cartridge body 1101 and slide the cover 1108 in a proximal direction relative to the assembly of the staple retainer 1106 and cartridge body 1101, in a manner similar to that as described above with reference to the embodiment of FIGS. 10A-10D. The downward and proximal direction movement of the cover 1108 causes transverse portions 1114 of the T-shaped projection 1113 to clear the inwardly extending lateral projections 1115 and allow removal of cover 1108 from the stapler reload cartridge body 1101.

FIG. 11C shows the assembly of the staple retainer 1106 and the cartridge body 1101, the cover 1108 having already been removed. Staple retainer 1106 can be removed from the cartridge body 1101 by applying an upward force on pull tab 1107 of the staple retainer 1106. Doing so will disengage one or more snap features (not shown) and/or friction fit interfaces that removably secure the staple retainer 1106 to the cartridge body 1101.

Figure 11D:
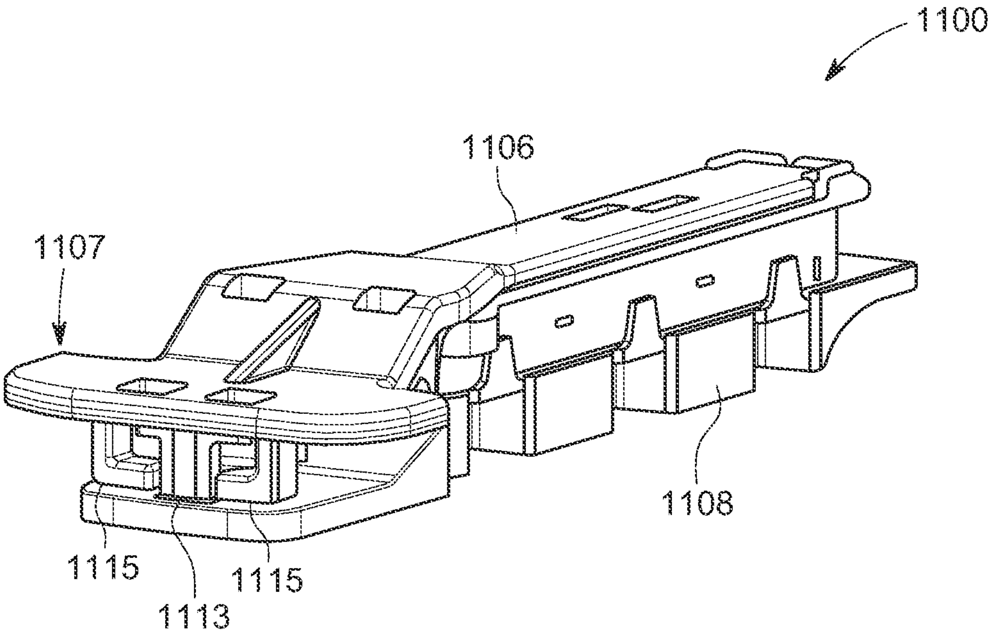
FIG. 11D is a perspective view of the stapler reload assembly of FIG. 11A in a fully assembled configuration.
Figure 11E:
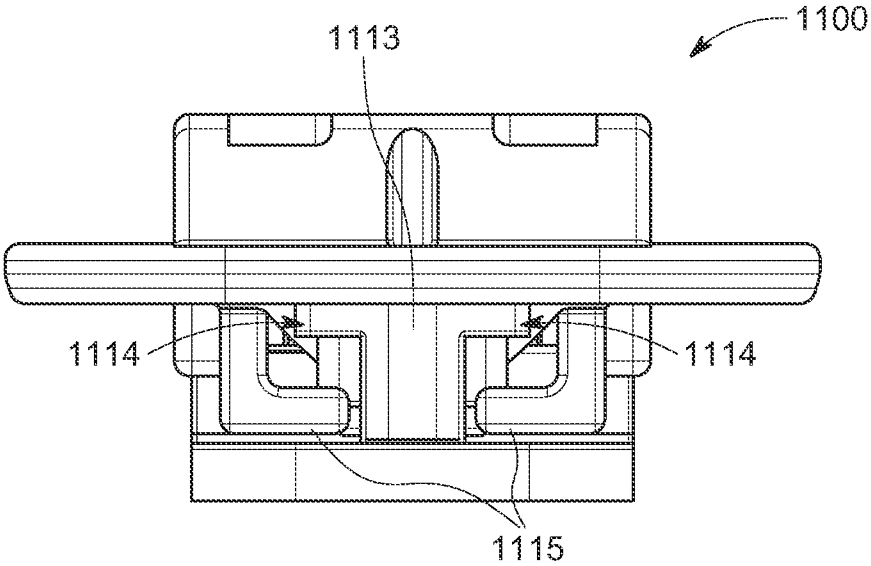
FIG. 11E is an end view of the stapler reload assembly of FIG. 11A taken through section 11-E shown in FIG. 11A.

FIG. 11D shows the stapler reload assembly 1100 in a fully assembled configuration from a perspective view. FIG. 11E shows an end view of the distal end of the stapler reload assembly in a fully assembled configuration. Both FIGS. 11D and 11E show the mechanical interface between the distal ends of the staple retainer 1106 and the cover 1108. When fully assembled, transverse portions 1114 of the cover 1108 are designed to interface with inwardly extending lateral projections 1115 to prevent the staple retainer 1106 from being removed from the cartridge body 1101 without first removing the cover 1108. If a user attempts to remove the staple retainer 1106 by applying an upward force F2 to pull tab 1107 of staple retainer 1106, the transverse portions 1114, which are positioned on top of inwardly extending lateral projections 1115 of the staple retainer 1106, will engage the transverse portions 1114 and resist the application of force F2. When stapler reload assembly 1100 is in its fully assembled configuration (as shown in FIG. 11A), the cover 1108 is secured to the cartridge body 1101 and the transverse portions 1114 are positioned directly above the inwardly extending lateral projections 1115 of the staple retainer 1106, preventing the staple retainer 1106 from being removed from the cartridge body 1101.

FIGS. 12A-12D show another embodiment of a stapler reload assembly 1200. Stapler reload assembly 1200 includes a cartridge body 1201, a staple retainer 1206, and a cover 1208. The staple retainer 1206 is removably secured to the cartridge body 1201 through one or more snap features (not shown) and/or friction fit interfaces. The cover 1208 is removably secured to the cartridge body 1201 via engagement of a plurality of retention tabs 1232 that positively engage with corresponding detents 1234 located on an outer surface of the cartridge body 1201.

Stapler reload assembly 1200 is designed to encourage an ordered sequence of removal of the cover 1208 from the cartridge body 1201 before removal of the staple retainer 1206 from the cartridge body 1201. This functionality is enabled by a recess 1216 (best shown in FIG. 12D) of the cover 1208, in which a pull tab 1207 of the staple retainer 1206 is countersunk when stapler reload assembly 1200 is in its fully assembled state, with the cover 1208 and stapler retainer 1206 in place. This countersinking makes it difficult to access pull tab 1207 of the staple retainer 1206 when the cover 1208 is installed on cartridge body 1201. Moreover, a pull tab of 1217 of cover 1208 extends beyond a distal dip of pull tab 1207 of the staple retainer 1206, which arrangement encourages grasping of the pull tab 1217 to first remove the cover 1208 from the cartridge body 1201 before removing the staple retainer 1206 from the cartridge body 1201 using the pull tab 1207.

Figure 12A:
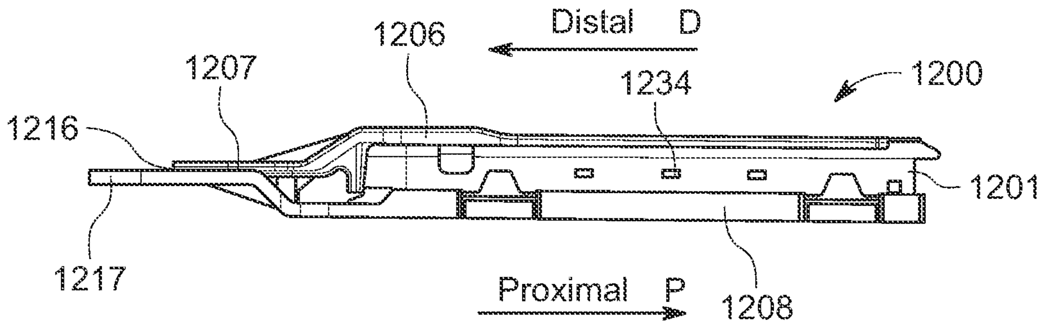
FIG. 12A is a side elevation view of a stapler reload assembly in a fully assembled configuration with a cover and retainer in place according to an exemplary embodiment of the present disclosure.
Figure 12B:
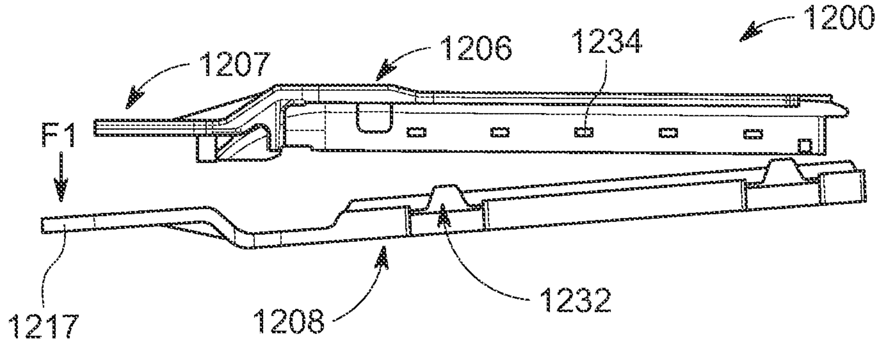
FIG. 12B is a side elevation view of the stapler reload assembly of FIG. 12A in a partly assembled configuration with the cover partially removed.
Figure 12C:
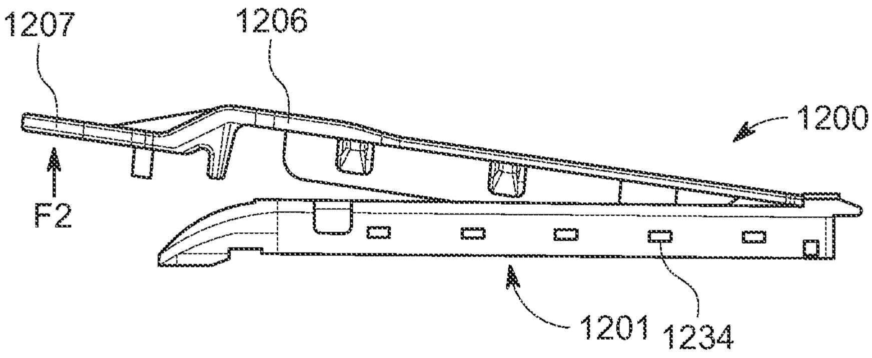
FIG. 12C is a side elevation view of the stapler reload assembly of FIG. 12B in a partly assembled configuration with the cover removed and the retain partially in place.

FIGS. 12A-12C show an exemplary workflow for preparing the stapler reload assembly 1200 for use. FIG. 12A shows stapler reload assembly 1200 in a fully assembled configuration. As can be seen, the pull tab 1217 of the cover 1208 extends further distally than the pull tab 1207 of the staple retainer 1206. A portion of the pull tab 1207 is countersunk into the recess 1216 of the pull tab 1217 (see also FIG. 12D), which arrangement makes access to the pull tab 1207 difficult if the cover 1208 is in place on the stapler reload cartridge body 1201.

FIG. 12B shows the stapler reload assembly 1200 in a partly disassembled configuration. In FIG. 12B, the cover 1208 is being removed from the assembly of the cartridge body 1201 and the staple retainer 1206. Removal of the cover 1208 is accomplished by applying a downward force F1 to the pull tab 1217. Doing so will disengage the retention tabs 1232 from the detents 1234 of cartridge body 1201 and fully expose retainer 1206's pull tab 1207 from cover 1208's recess 1216. A user can now access pull tab 1207.

FIG. 12C shows the assembly of staple retainer 1206 and cartridge body 1201, the cover 1208 having already been removed. The staple retainer 1206 can be removed from the cartridge body 1201 by applying an upward force F2 to the pull tab 1207 of the staple retainer 1206. Doing so will disengage the one or more snap features (not shown) and/or friction fit interfaces that removably secure the staple retainer 1206 to the cartridge body 1201 and separate the staple retainer 1206 from the cartridge body 1201.

Figure 12D:
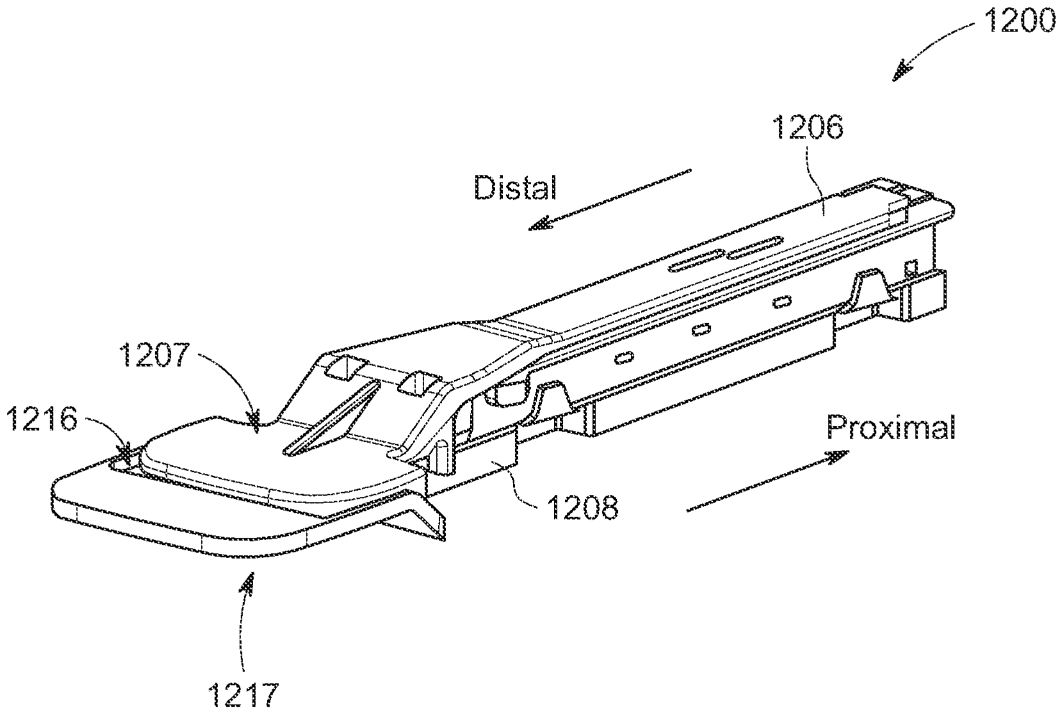
FIG. 12D is a perspective view of the stapler reload assembly of FIG. 12A.

FIG. 12D shows the stapler reload assembly 1200 in a fully assembled configuration from an isometric view. When stapler reload assembly 1200 is in a fully assembled configuration, the pull tab 1207 of the staple retainer 1206 is countersunk into the recess 1216 of the cover 1208. This countersinking makes it difficult for a user to access the pull tab 1207 of the staple retainer 1206 when the cover 1208 is still installed on the cartridge body 1201. Moreover, a pull tab of 1217 of the cover 1208 extends beyond a distal tip of pull tab 1207 of the staple retainer 1206, encouraging a user to first remove the cover 1208 from the cartridge body 1201 using the pull tab 1217 before removing the staple retainer 1206 from the cartridge body 1201 using the pull tab 1207.

Figure 13A:
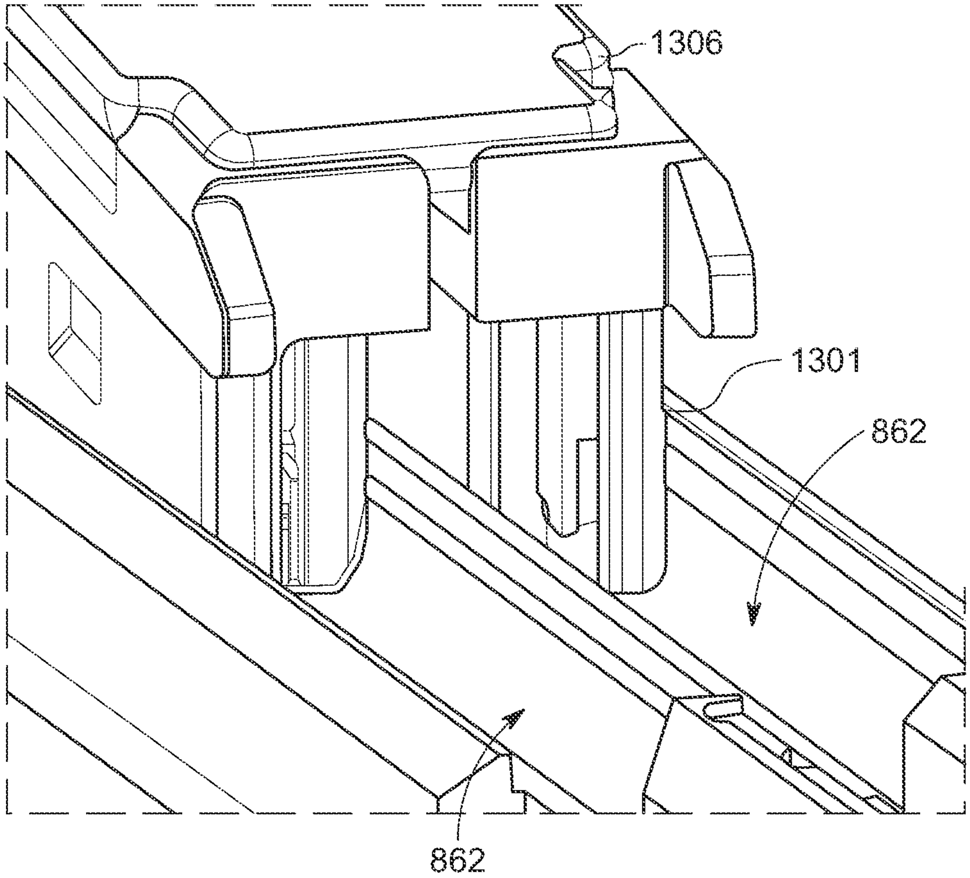
FIG. 13A is a detailed, partial, perspective view of an exemplary cartridge-retaining jaw of a surgical instrument according to an exemplary embodiment of the present disclosure.

Referring again to FIG. 8, cartridge-retaining jaw 860 includes channels 862 configured to accept corresponding portions of a stapler reload cartridge body as described above. To facilitate installation of a cartridge body into cartridge-retaining jaw 860, it can be helpful if the corresponding portions of a cartridge body sized for insertion into channels 862 are properly spaced to be installed into the channels 862 of cartridge-retaining jaw 860. FIG. 13A shows the installation of the combination of a cartridge body 1301 and staple retainer 1306 into cartridge-retaining jaw 860. Note the alignment of the downward-projecting features of cartridge body 1301 with the channels 862 of the cartridge-retaining jaw 860. In various embodiments, a staple retainer can include features that assist to properly space legs of a cartridge body as discussed above.

Figure 13B:
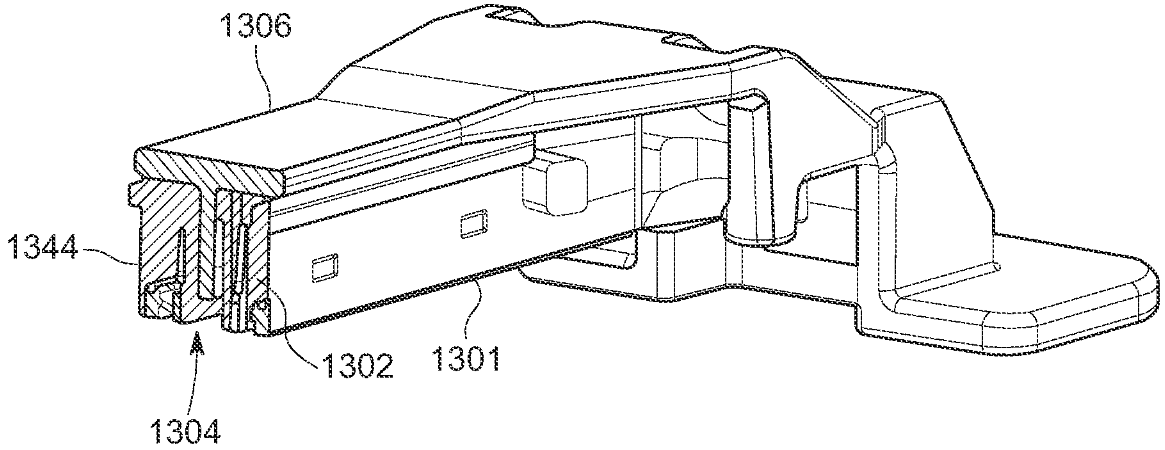
FIG. 13B is a cross-sectional view of a stapler reload cartridge and staple retainer according to an exemplary embodiment of the present disclosure.

FIG. 13B shows a cross sectional view of the assembly of the cartridge body 1301 and the staple retainer 1306. Specifically, it shows a septum 1344 of the staple retainer 1308 that extends downward into a slot 1304 defined by the cartridge body 1301. The septum 1344 engages with legs 1302 of the cartridge body 1301 to ensure that the legs 1302 are held at a predetermined spacing from one another. This way, when the assembly of cartridge body 1301 and staple retainer 1306 is installed into cartridge-retaining jaw 860, the legs 1302 of cartridge body 1301 will slide into the channels 862 defined by the cartridge-retaining jaw 860. Once the assembly of the cartridge body 1301 and the staple retainer 1306 is installed into the cartridge-retaining jaw 860, the staple retainer 1306 can be removed from the cartridge body 1301 in a manner similar to that described elsewhere herein in relation to other exemplary embodiments.

Many of the exemplary embodiments of staple cartridge assemblies discussed herein include various features that provide some degree of mechanical engagement between the cover and staple retainer. However, some stapler reload cartridge assemblies according to the present disclosure do not include such engagement features. Such exemplary embodiments can nonetheless be con to encourage an ordered sequence of removal of the cover prior to removal of the staple retainer from the stapler reload cartridge body.

For example, some stapler reload assembly designs encourage a user to remove the cover before the staple retainer by requiring that a force applied to remove the staple retainer be higher than a force required to remove the cover. Such designs can also include features that direct a user to manipulate the stapler reload assembly in such a manner as to ensure that the cover releases from the stapler reload cartridge body prior to the staple retainer releasing from the stapler reload cartridge body. As used herein, the term "retention force" can be or include a force required to be applied to the staple retainer or the cover to remove the staple retainer or cover from the stapler reload cartridge body.

FIGS. 14-20 show various views of a stapler reload assembly 1450. The stapler reload assembly 1450 includes a cartridge body, a staple retainer, and a cover, and the staple retainer requires a greater force to remove than the cover.

Figure 14:
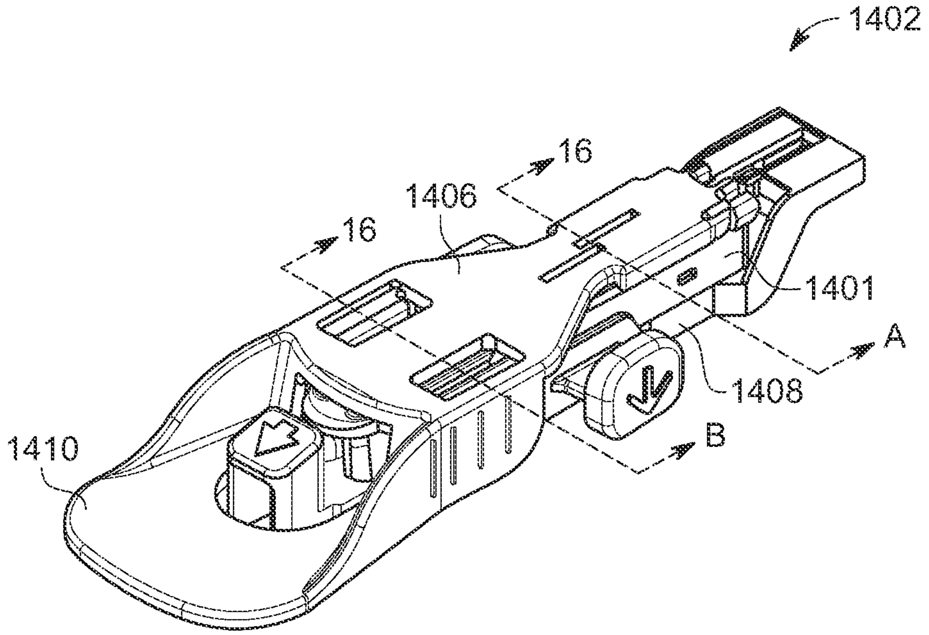
FIG. 14 is a perspective view of a stapler reload assembly in a fully assembled configuration with a cover and retainer in place according to another exemplary embodiment of the present disclosure.

Referring to FIG. 14, the stapler reload assembly 1450 includes a staple retainer 1406 installed over and covering at least a portion of a staple ejection side (e.g., staple ejection side 211 of stapler reload cartridge 200 in FIG. 2) and a cover 1408 installed over and covering at least a portion of a pusher loading side (e.g., a pusher loading side 213 of stapler reload cartridge 200 in FIG. 2) of a cartridge body 1401. The staple retainer 1406 includes a handling portion 1410 that provides a surface that is easy to grasp when holding the stapler reload assembly 1450 and when installing and removing the stapler reload assembly 1450 in a stapler instrument.

Figure 15A:
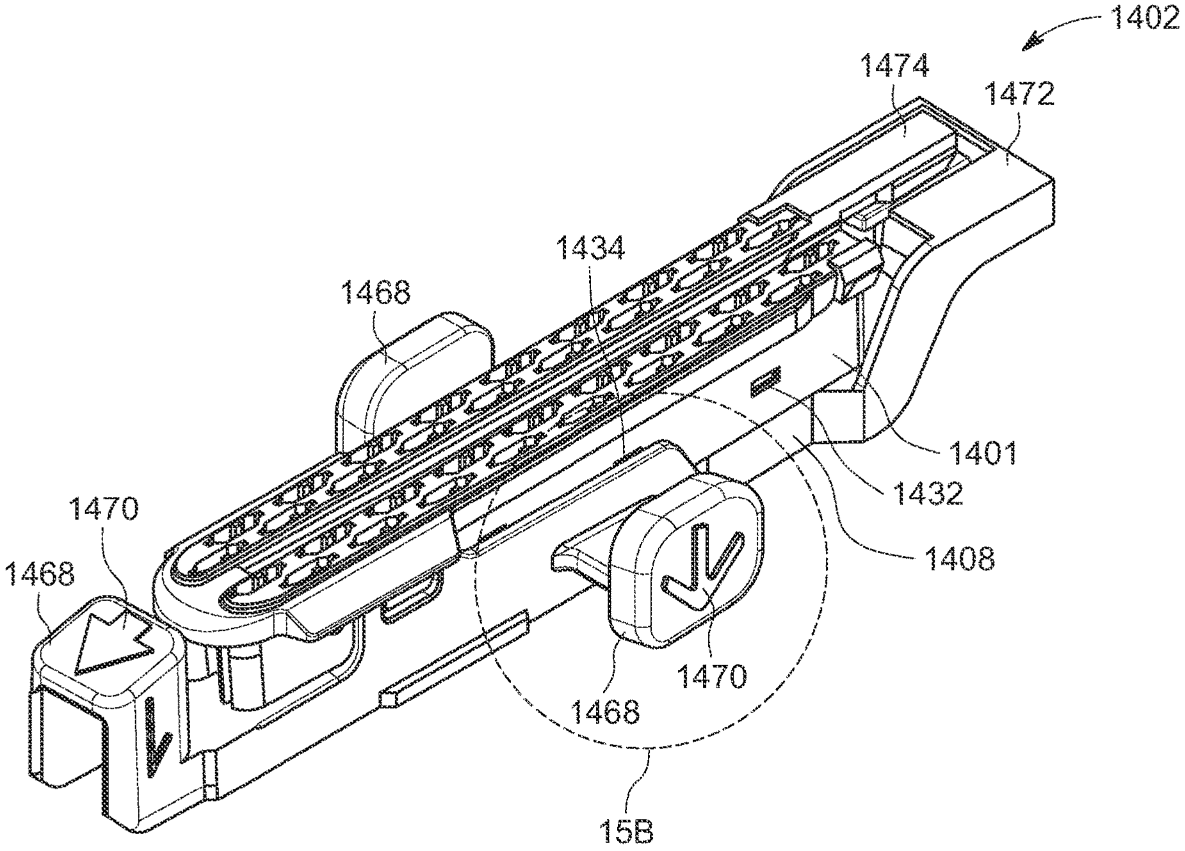
FIG. 15A is a perspective view of the stapler reload assembly of FIG. 14 in a partially assembled configuration with the retainer removed.
Figure 15B:
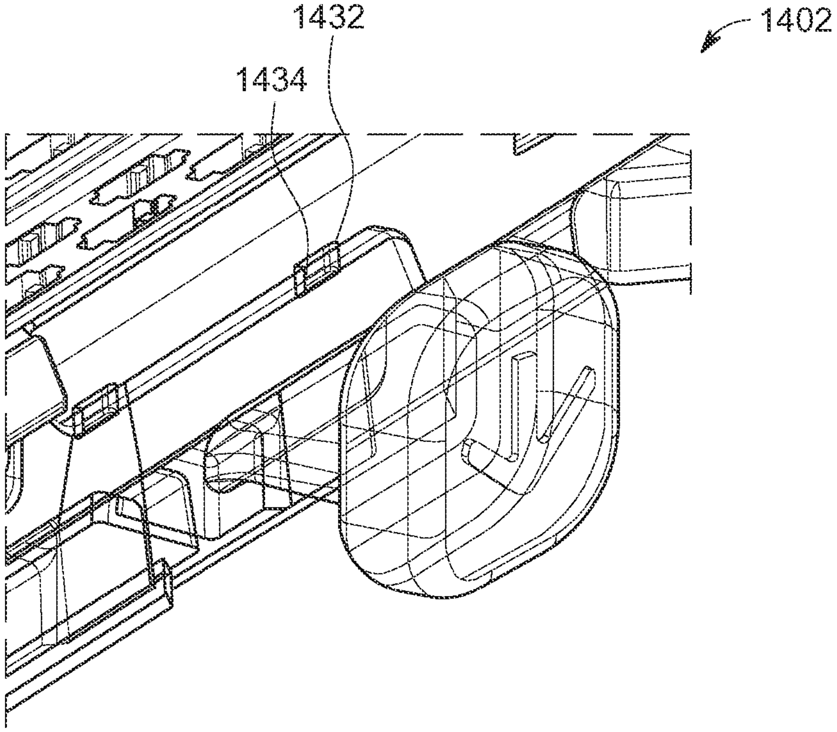
FIG. 15B is a detailed view of the portion 15-B of the stapler reload assembly of FIG. 15A.
Figure 15C:
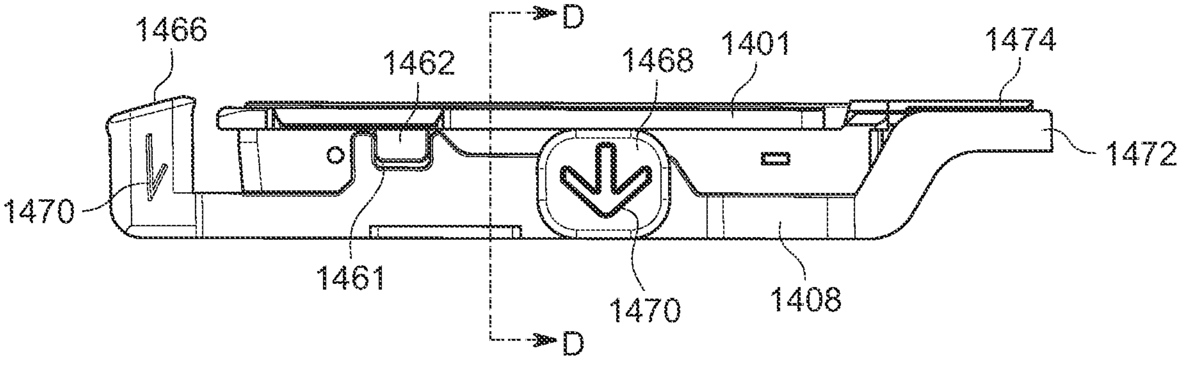
FIG. 15C is a side elevation view of the stapler reload assembly of FIG. 15A in a fully assembled configuration with a cover and retainer in place.

Referring now to FIG. 15A, a perspective view of the stapler reload assembly 1450 is shown, with the staple retainer 1406 (FIG. 14) omitted to better show various features of the cover 1408 and cartridge body 1401. The cover 1408 and the cartridge body 1401 include interacting features that retain the cover 1408 to the cartridge body 1401 independently of the staple retainer 1406 (FIG. 14). For example, such features can include snap-fit features, interference fit features, or other types of mechanically engageable features. In the exemplary embodiment of FIGS. 14-16B, the cartridge body 1401 includes one or more detents 1432 in a side portion of the cartridge body 1401. The cover 1408 includes one or more retention tabs 1434 that are received within the one or more detents 1432 of the cartridge body 1401 to retain the cover 1408 on the cartridge body 1401. FIG. 15B shows an enlarged view of the cover 1408 and cartridge body 1401 to better illustrate the detents 1432 and retention tabs 1434 received therein.

The cover 1408 and the cartridge body 1401 can include additional features that assist in a desired positioning of the cover 1408 relative to the cartridge body 1401, such as in a longitudinal direction. For example, as shown most clearly in FIG. 15C, the cover 1408 includes notches 1461. The cartridge body 1401 includes keys 1462 configured to be received into the notches 1461 to longitudinally position the cover 1408 relative to the cartridge body 1401.

Figure 15D:
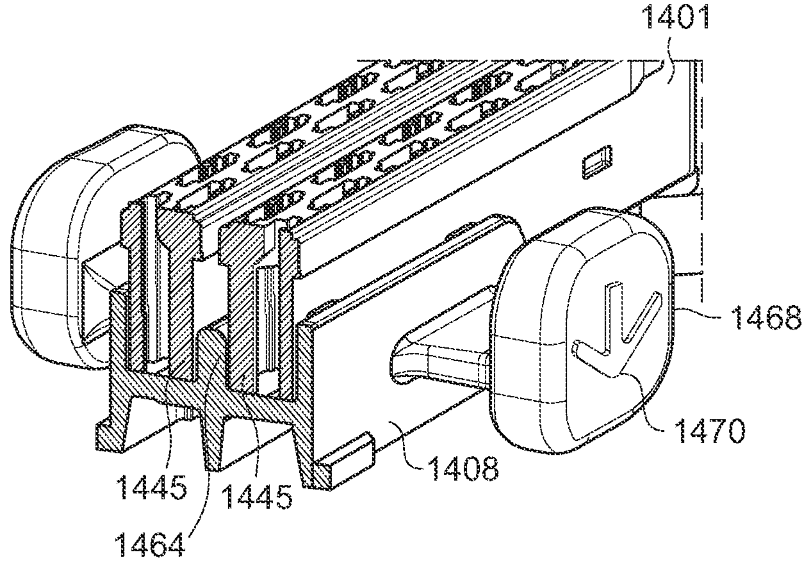
FIG. 15D is a partial perspective cross-sectional view of the assembly of FIG. 15A taken through 15-D of FIG. 15C.

Referring now to FIG. 15D, the cover 1408 can also include one or more features that maintain a lateral position of legs 1445 of the cartridge body 1401 relative to one another. For example, the cover 1408 includes a spacer element 1464 that protrudes between legs 1445 of the cartridge body 1401. The spacer element 1464 prevents deflection of unsupported lengths of the cartridge body 1401 as discussed in connection with, for example, FIGS. 3A and 13B herein.

The cover 1408 includes one or more features to facilitate removal of the cover 1408. Such features can include markings or other indicia that indicate how to remove the cover 1408. For example, the cover 1408 includes a distal button 1466 and two lateral extensions 1468. One or more of the distal button 1466 and the two lateral extensions 1468 can include markings indicating how to remove the cover 1408, such as, for example, the arrow markings 1470. Removal of the cover 1408 is discussed further herein in connection with FIGS. 17A-17C. The two lateral extensions 1468 can also serve to prevent the stapler reload assembly 1450 from inadvertently being dropped down a cannula through which the stapler instrument or other instruments are inserted.

The cover 1408 can include various other features to protect (e.g., cover) other components of the cartridge body 1401. For example, in some exemplary embodiments, the cover 1408 can include a proximal portion 1472 that at least partially surrounds an identification element 1474 of the cartridge body 1401. The identification element 1474 can be or include, without limitation, identification elements and related structures such as those disclosed in detail in Int'l Patent App. Pub. Nos. WO2020/131685 (filed Dec. 16, 2019) titled SURGICAL INSTRUMENTS WITH SWITCHES FOR DEACTIVATING AND/OR IDENTIFYING STAPLER CARTRIDGES and WO2020/131692 (filed Dec. 16, 2019) titled SURGICAL INSTRUMENTS HAVING MECHANISMS FOR IDENTIFYING AND/OR DEACTIVATING STAPLER CARTRIDGES, the entire contents of each of which are incorporated by reference herein. The proximal portion 1472 of the cover 1408 is positioned to protect the identification element 1474 of the cartridge body 1401 from damage resulting from handling of the cartridge body 1401.

Figure 16A:
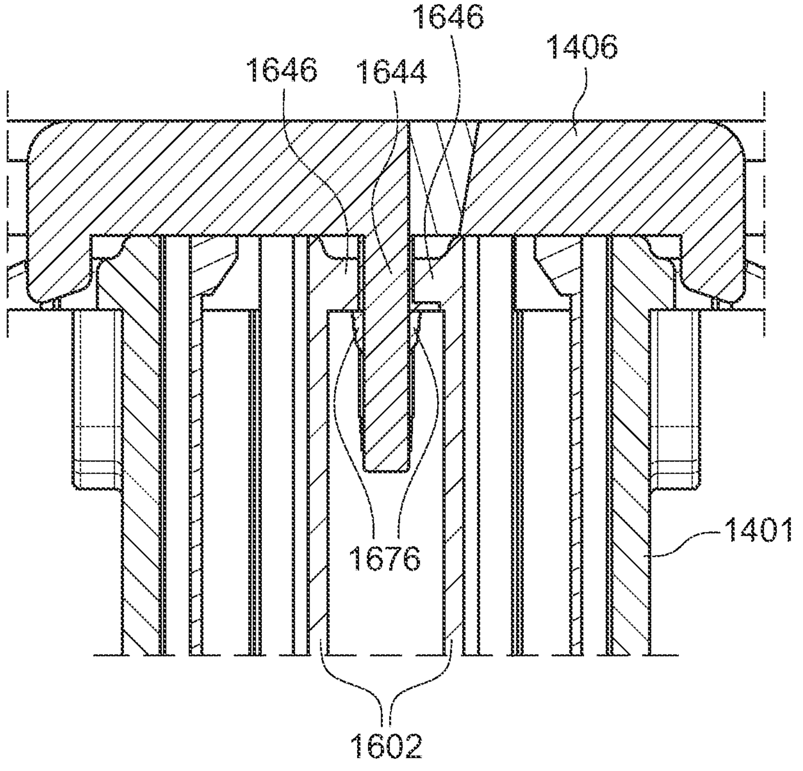
FIG. 16A is a cross-sectional view of the stapler reload assembly taken through cross-section 16-A in FIG. 14 with the cover removed
Figure 16B:
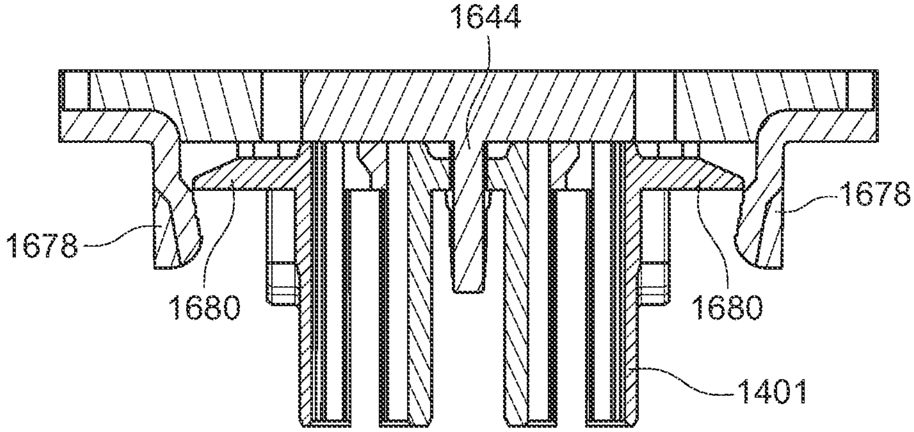
FIG. 16B is another cross-sectional view of the stapler reload assembly taken through cross-section 16-B in FIG. 14 with the cover removed.

The staple retainer 1406 (FIG. 14) includes features to retain the staple retainer 1406 on the cartridge body 1401. As discussed above, the features can be configured such that a force required to remove the staple retainer 1406 from the cartridge body 1401 is greater than a force required to remove the cover 1408 from the cartridge body 1401. FIGS. 16A-16C show various lateral cross-sectional views of the cartridge body 1401 with the staple retainer 1406 in place and the cover 1408 omitted.

FIG. 16A shows a transverse cross-sectional view of the cartridge body 1401 and the staple retainer 1406 (with cover 1408 omitted for clarity) along section 16-A-16-A indicated in FIG. 14. The staple retainer 1406 includes a septum 1644 extending between legs 1602 of the stapler reload cartridge body 1401. The septum 1644 prevents deflection of the legs 1602 relative to one another, as discussed further in connection with FIGS. 3A and 13B. The septum 1644 can include features that retain the staple retainer 1406 on the stapler reload cartridge body 1401. For example, in the exemplary embodiment of FIG. 16A, the septum 1644 includes tabs 1676 that create an interference fit with flanges 1646 of the cartridge body 1401. An interference fit between the tabs 1676 and the flanges 1646 at least partially retains the staple retainer 1406 on the cartridge body 1401.

The staple retainer 1406 can include additional features that interact with the cartridge body 1401 to retain the staple retainer 1406 on the cartridge body 1401. For example, referring now to FIG. 16B, which shows a transverse cross-sectional view along 16-B-16-B shown in FIG. 14 (with cover 1408 again omitted for clarity), the staple retainer 1406 includes projections 1678. The cartridge body 1401 includes laterally-extending wings 1680, and the projections 1678 engage the wings 1680 when the staple retainer 1406 is in place on the cartridge body 1401. The combination of the septum 1644 and projections 1678 together retain the staple retainer 1406 in place on the cartridge body 1401.

Figure 17A:
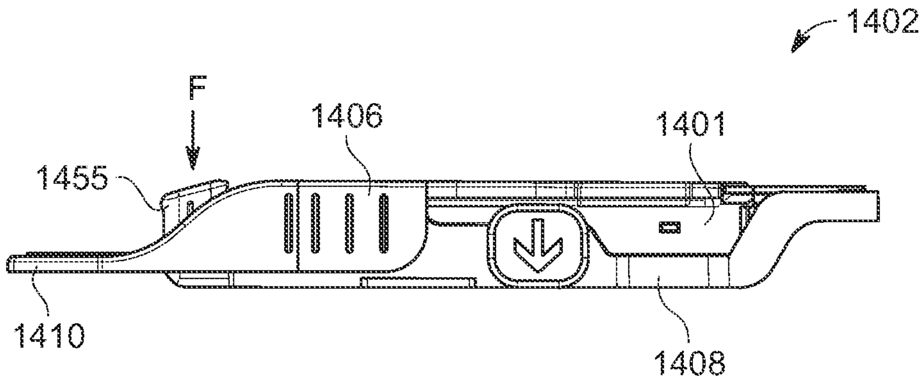
FIG. 17A is a side elevation view of the stapler reload assembly of FIG. 14 in a fully assembled configuration with the retainer and the cover in place.
Figure 17B:
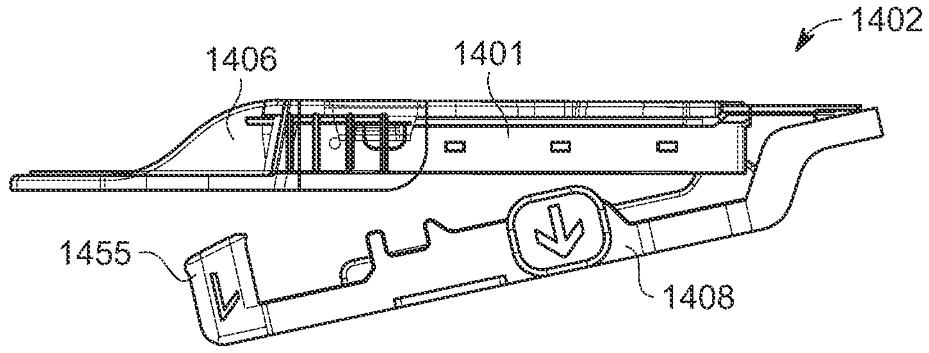
FIG. 17B is a side elevation view of the stapler reload assembly of FIG. 17A in a partly disassembled configuration with the cover partially removed.

FIGS. 17A and 17B illustrate a "one handed" method of removing the cover 1408 from the cartridge body 1401. FIG. 17A shows the stapler reload assembly 1450 in a fully assembled state. A user can grasp the handling portion 1410 of the staple retainer 1406 in one hand, and with the thumb of the one hand, apply a force F to the distal button 1455. The force F is sufficient to overcome a retention force of the cover 1408 (e.g., a first retention force) on the cartridge body 1401 provided by the detents 1432 and retention tabs 1434 discussed above in connection with FIGS. 15A and 15B, but is not sufficient to overcome a retention force holding the staple retainer 1406 (e.g., a second retention force) in place on the cartridge body 1401. As a result, the retention tabs 1434 disengage from the detents 1432, and the cover 1408 drops away from the cartridge body 1401, as shown in FIG. 17B.

Figure 18A:
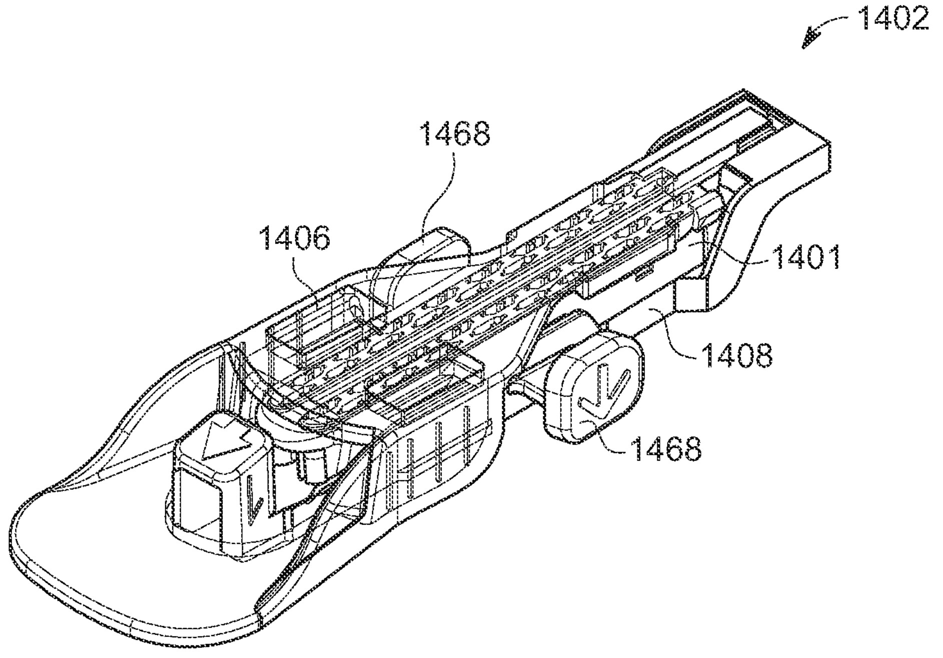
FIG. 18A is a perspective view of the stapler reload assembly of FIG. 14 with portions of the retainer transparent to depict interior components of the assembly.
Figure 18B:
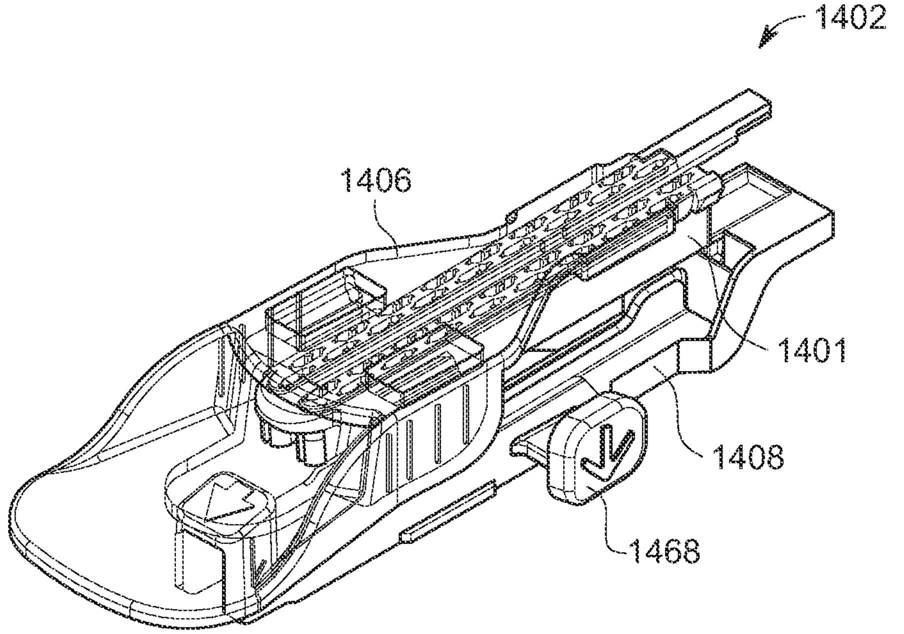
FIG. 18B is a perspective view of the stapler reload assembly of FIG. 18A in a partly disassembled configuration with the cover partially removed.

As an alternative to the one-handed removal described in connection with FIGS. 17A and 17B, a user can remove the cover 1408 using a two-handed method. Referring to FIG. 18A, the stapler reload assembly 1450 is shown again in an assembled state. To remove the cover 1408, a user can grasp the stapler reload assembly 1450 with one hand and pull on the cover 1408 by the two lateral extensions 1468, causing the retention tabs 1434 to disengage from the detents 1432, releasing the cover 1408 from the cartridge body 1401.

Figure 19:
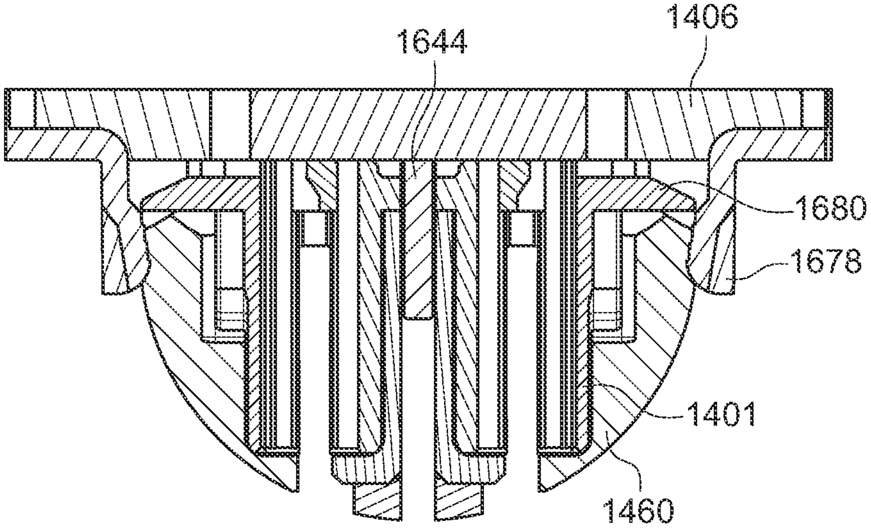
FIG. 19 is a cross-sectional view of a stapler reload cartridge with a staple retainer of FIG. 18B installed in a cartridge-retaining jaw of a stapler instrument according to an exemplary embodiment of the present disclosure.

Once the cover 1408 is removed from the stapler reload cartridge body 1401, either by the one-handed or two-handed approach, the cartridge body 1401 is ready to be inserted in the stapler instrument. Referring now to FIG. 19, a cross-sectional view of the cartridge body 1401 with the staple retainer 1406 still in place is shown installed in a cartridge-retaining jaw 1460 (similar to cartridge-retaining jaw 860 discussed above in connection with FIG. 8, but including additional features as discussed further below with reference to FIG. 20).

The staple retainer 1406 can be designed to interact with the cartridge-retaining jaw 1460 in various ways to facilitate removal of the staple retainer 1406 from the cartridge body 1401 when the cartridge body 1401 is installed in the cartridge-retaining jaw 1460. For example, as shown in FIG. 19, the projections 1678 are pushed outward by interference with the cartridge-retaining jaw 1460 such that the projections 1678 partially or fully clear the wings 1680. The user can then remove the staple retainer 1406 from the cartridge body 1401 by applying enough force to overcome the retention force of the tabs 1676 (FIG. 16A) of the septum 1644 and any interference between the projections 1678 and the wings 1680 not overcome by contact between the projections 1678 and the cartridge-retaining jaw 1460. The staple retainer 1406 is thereby released from the cartridge body 1401, and the stapler reload cartridge is prepared for use.

Figure 20:
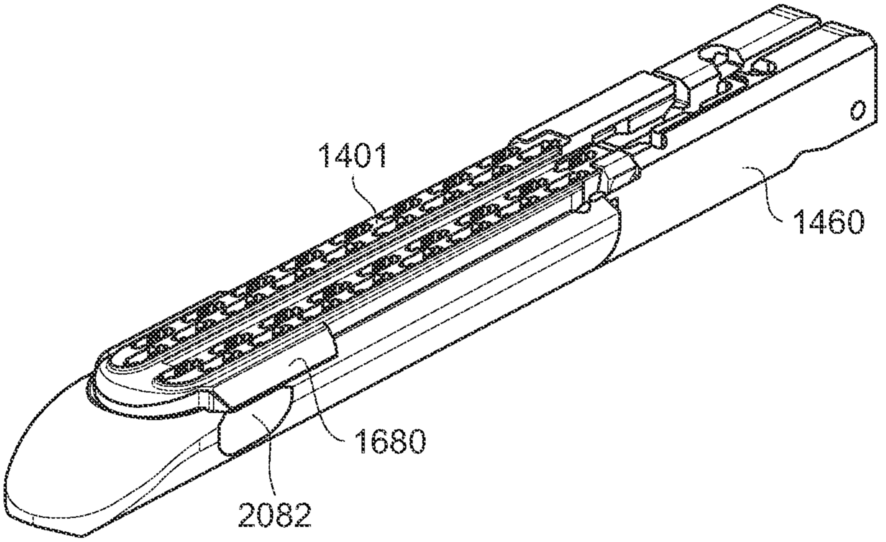
FIG. 20 is a perspective view of a stapler reload cartridge installed in a jaw of a stapler instrument according to an exemplary embodiment of the present disclosure.

FIG. 20 shows a cartridge body 1401 installed in a cartridge-retaining jaw 1460. The cartridge-retaining jaw can include features that interact with features of the stapler reload cartridge body to facilitate removal of the cartridge body following use of the stapler instrument in preparation for cleaning, installation of a new stapler reload cartridge, etc. For example, the cartridge-retaining jaw 1460 can include at least one relief 2082 in a lateral side of the cartridge-retaining jaw 1460, located such that the wings 1680 of the cartridge body 1401 at least partially overhang the cartridge-retaining jaw 1460 at the relief 2082. The overhanging portion of the wings 1680 can provide a location for the user to grip the cartridge body 1401 to remove it from the cartridge-retaining jaw 1460 after use of the stapler instrument. In the exemplary embodiment of FIG. 20, the cartridge-retaining jaw 1460 includes two reliefs 2082 on opposite sides of the cartridge-retaining jaw 1460, of which only one is shown. Other embodiments may include a lesser or greater number of reliefs 2082, and the configuration of the reliefs 2082 may vary from that shown in FIG. 20 while remaining within the scope of the disclosure.

The various engagement and retaining features described in the present disclosure are generally configured to produce mating fits, such as, but not limited to, snap fits, friction fits, interference fits, etc. One of ordinary skill in the art would appreciate that that various protrusions and recesses or male/female type engagement features on different parts could be reversed or otherwise changed in configuration from the particular configurations described herein without departing from the scope of the present disclosure.

Figure 21:
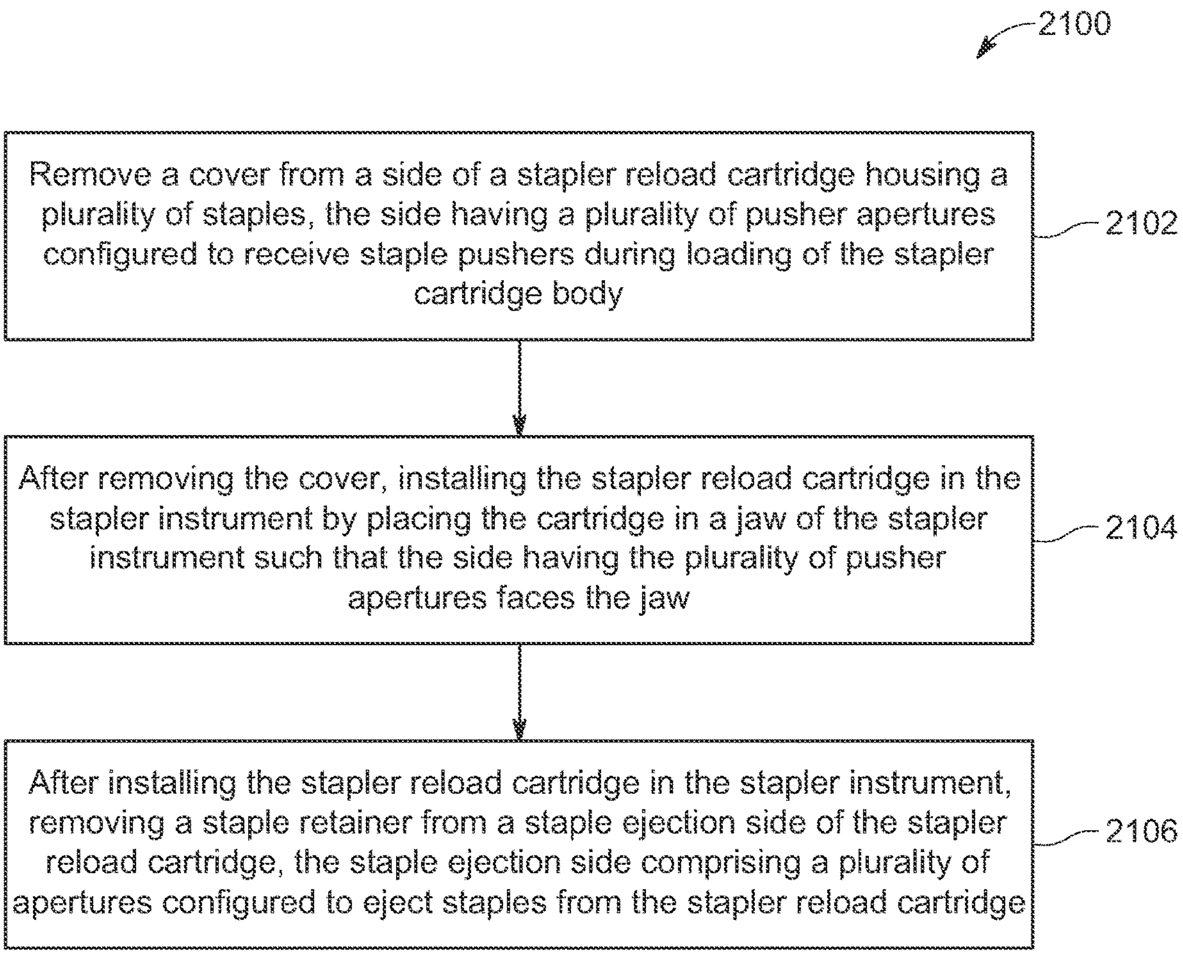
FIG. 21 illustrates an exemplary workflow for preparation and insertion of a stapler reload assembly into a stapler instrument.

Referring now to FIG. 21, a workflow 2100 for preparing a stapler reload assembly for use is shown. At 2102, a cover is removed from a staple ejection side of a stapler reload cartridge housing a plurality of staples, the side having a plurality of pusher apertures configured to receive staple pushers during loading of the stapler cartridge body. The cover can correspond, without limitation, to the various exemplary embodiments of covers discussed herein. At 2104, after removing the cover, the stapler reload cartridge is installed in the stapler instrument by placing the cartridge in a jaw of the stapler instrument such that the side having the plurality of pusher apertures faces the jaw. The stapler reload cartridge can correspond without limitation to embodiments of stapler reload cartridges discussed herein. At 2106, after installing the stapler reload cartridge in the stapler instrument, a staple retainer is removed from the staple ejection side of the stapler reload cartridge. The staple ejection side comprises a plurality of staple apertures configured to eject staples from the stapler reload cartridge. The staple retainer can correspond, without limitation, to the various exemplary embodiments of staple retainers discussed herein.

Various other embodiments of the disclosure, components of stapler reload cartridge assemblies can include features that facilitate a user's application of force to seat the stapler reload cartridge in the stapler instrument. In some embodiments, staple retainers have structures that exert force to keep the stapler reload cartridge seated in the stapler jaw of a stapler instrument while the staple retainer is being removed from the stapler reload cartridge.

Figure 22:
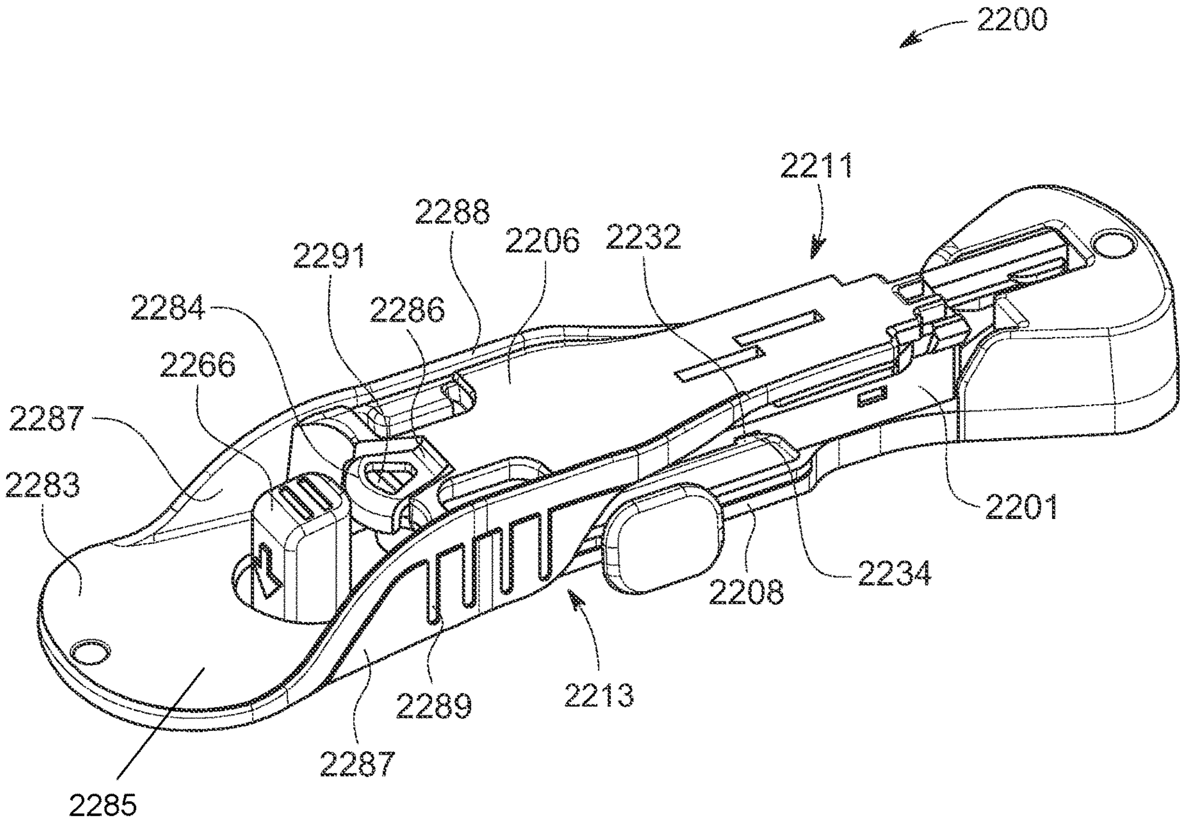
FIG. 22 is a perspective view of a stapler reload assembly in a fully assembled configuration with a cover and retainer in place according to another exemplary embodiment of the present disclosure.
Figure 23A:
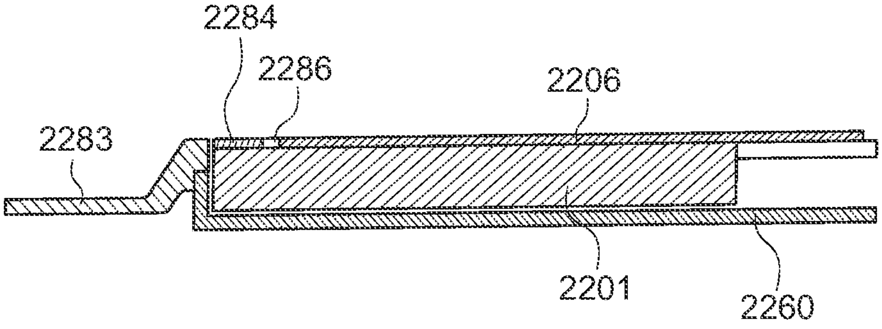
FIGS. 23A and 23B are schematic, side cross-sectional views of the stapler reload assembly of FIG. 22 with its cover removed and partially installed in a cartridge-retaining jaw of a stapler instrument.
Figure 23B:
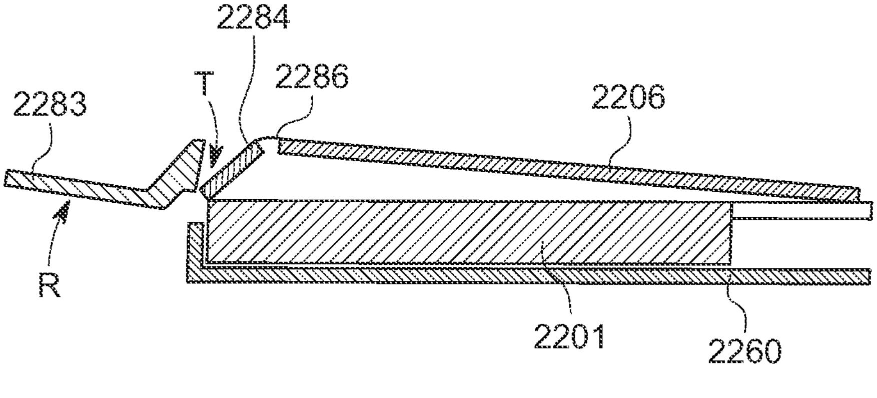

In the embodiment of FIGS. 22-23B below, a staple retainer of a stapler reload assembly includes a handling system configured and arranged to facilitate an application of force to keep the stapler reload cartridge seated in the stapler instrument jaw as the staple retainer is disengaged during removal from the stapler reload cartridge. Referring to FIG. 22, a side perspective view of another embodiment of a stapler reload assembly 2200 is shown. The stapler reload assembly 2200 includes a stapler reload cartridge body 2201, a staple retainer 2206, and a cover 2208. The staple retainer 2206 is removably coupled to the stapler reload cartridge body 2201 to cover a staple ejection side 2211 of the stapler reload cartridge body 2201. The cover 2208 is removably coupled to the stapler reload cartridge body 2201 to cover a pusher loading side 2213 of the stapler reload cartridge body 2201 opposite the staple ejection side 2211 of the stapler reload cartridge body 2201.

Various features of the stapler reload assembly 2200, the staple retainer 2206, and the cover 2208 are similar to the features discussed in connection with the exemplary embodiments of FIGS. 14-20, including various features of the staple retainer 2206 and cover 2208 that interact with the stapler reload cartridge body 2201 to retain the staple retainer 2206 on the cartridge body and retain the cover 2208 on the cartridge body 2201. For example, the staple retainer 2206 can include a septum (not shown in FIG. 22; similar to septum 1644 shown and disclosed in connection with FIGS. 16A, 16B and 19) with or without tabs (not shown in FIG. 22; similar to tabs 1676 shown and disclosed in connection with FIG. 16A) configured to engage the stapler reload cartridge body 2201. The cover 2208 can include retention tabs 2234 (similar to the retention tabs 1434 shown and disclosed in connection with FIG. 15B) that engage detents 2232 (similar to detents 1432 shown and described in connection with FIG. 15B) in the stapler reload cartridge body 2201. In addition, the staple retainer 2206 and/or cover 2208 can include any or all of the various engagement features and interacting features discussed in connection with exemplary embodiments of the present disclosure. For simplicity, the various features of FIGS. 14-20 are not all shown and discussed in connection with the embodiment of FIGS. 22-23B, but those have ordinary skill in the art would appreciate the features in common between the embodiments or that could be included in FIGS. 22-23B even though not specifically discussed here.

In the exemplary embodiment of FIG. 22, the staple retainer 2206 has a handling system that includes a first handling portion 2283 generally forming a distal end portion of the staple retainer 2206. The first handling portion 2283 can be similar to the handling portion 1410 disclosed in connection with the embodiment of FIGS. 14-20. The first handling portion 2283 features a generally paddle-shaped gripping area 2285 between lateral walls 2287 that extend generally perpendicular to the gripping area 2285. The gripping area 2285 and lateral walls 2287 provide multiple surfaces to facilitate manipulation and handling of the stapler reload assembly 2200. The lateral walls 2287 and/or the gripping area 2285 can include additional features configured to improve grip, such as grooves 2289. Other surface features or textures, such as, for example and not by limitation, knurling, pebbling, cross-hatching, and other features can optionally be included on the lateral walls 2287 and/or gripping area 2285. In addition, the staple retainer 2206 includes ridges 2288 that extend longitudinally along a portion of the staple retainer 2206. The ridges 2288 contribute to overall stiffness of the staple retainer 2206 by increasing the area moment of inertia along a longitudinal axis of the staple retainer 2206. The arrangement shown in FIG. 22 can contribute to reducing unwanted deflection of the staple retainer 2206 along the longitudinal axis, e.g., during removal of the staple retainer, while still allowing deflection of various portions as desired, such as lateral outward deflection of projections 1678 (FIGS. 16B and 19) so that projections 1678 disengage from wings 1680 (FIGS. 16B and 19) upon installation of the stapler reload cartridge body 2201, as discussed further in connection with FIGS. 16B and 19 and below. Those having ordinary skill in the art would appreciate other features configured to facilitate handling of the stapler reload assembly as discussed in connection with other embodiments disclosed herein can be provided on the staple retainer 2206.

The handling system of the staple retainer 2206 further comprises a second handling portion 2284 coupled at a distal end of the main body portion of the staple retainer 2206 that covers the staple ejection side of the staple cartridge body 2201. The second handling portion 2284 is attached to the main body portion by a flexure 2286 and extends distally from the flexure 2286 to present a seat for a user's thumb, as described further below. The flexure 2286 can be or comprise a living hinge, a mechanical hinge, spring member, or other flexible component, without limitation, that permits the second handling portion 2284 to be elastically flexed relative to the main body portion of the staple retainer 2206 as further described below. In the exemplary embodiment of FIG. 22, the second handling portion 2284 is molded integrally with the staple retainer 2206 and the flexure 2286 is a living hinge. As can be seen in FIG. 22, the second handling portion 2284 is located just proximal of the distal button 2266 of the cover 2208.

Because of the flexure 2286 connection, the second handling portion 2284 is configured to elastically deflect when force is applied during removal of the staple retainer 2206 from the stapler reload cartridge body once the cartridge body 2201 is seated in a cartridge-retaining jaw of a stapler instrument.

With reference now to FIG. 23A, a schematic, cross-sectional view of the stapler reload cartridge body 2201 being installed in a cartridge-retaining jaw 2260 of a stapler instrument is shown. Removal of the cover 2208 can occur in a manner similar to that described above in connection with the embodiment of FIGS. 14-20. Further, as mentioned above, the staple retainer embodiment of FIGS. 22, 23A, and 23B can include engagement features similar to those discussed in connection with the embodiment of FIGS. 14-20 that attach the staple retainer to the reload cartridge body. Accordingly, insertion of the stapler reload cartridge body 2201 in the cartridge-retaining jaw 2260 can result in disengagement of the engagement features as discussed in further detail in connection with the embodiment of FIGS. 14-20. For example, insertion of the stapler reload cartridge body 2201 in the cartridge-retaining jaw 2260 results in projections 1678 (FIGS. 16B and 19) of the staple retainer 2206 being deflected laterally outwardly and disengaging from wings 1680 (FIGS. 16B and 19) of the cartridge body 2201 as discussed in connection with FIGS. 16B and 19. Other embodiments of the stapler reload assembly can include additional or alternative engagement features, such as, without limitation, any of the engagement features discussed in connection with other embodiments disclosed herein.

Disengagement of the projections 1678 (FIGS. 16B and 19) from the wings 1680 (FIGS. 16B and 19) permits the staple retainer 2206 to be removed from the stapler reload cartridge body 2201. However, interaction (e.g., friction or interference) between various other components of the stapler reload cartridge body 2201 and staple retainer 2206 can result in the stapler reload cartridge body 2201 being pulled from the cartridge-retaining jaw 2260 with the staple retainer 2206 as an attempt is made to remove and separate the staple retainer 2206 from the stapler reload cartridge body 2201. For example, engagement of tabs 1676 of septum 1644 (FIGS. 16B and 19) with the stapler reload cartridge body 2201 and/or friction between the septum 1644 and the stapler reload cartridge body 2201 can result in the stapler reload cartridge body 2201 being unseated from the cartridge-retaining jaw 2260 as the user pulls the staple retainer 2206 away.

To ensure the stapler reload cartridge body 2201 remains seated within the cartridge-retaining jaw 2260 while the staple retainer 2206 is being removed, a force can be applied to the second handling portion 2284 during an initial stage of removal of the staple retainer 2206 from the stapler reload cartridge body 2201. More specifically, as a force R is being applied to the first handling portion 2283 of the staple retainer 2206 to remove it from the stapler reload cartridge body 2201, a force T can be applied to in a generally opposite direction to the second handling portion 2284. While force R and force T are discussed herein as being generally opposite one another in direction, and force R having some force component in a first direction and any force T having a force component in a second direction opposite the first direction can be considered forces in generally opposite directions. Application of the force T causes the second handling portion 2284 to deflect from the first configuration, shown in FIG. 23A, in which the second handling portion 2284 is generally in an unbiased (e.g., undeflected) neutral configuration, to the second configuration shown in FIG. 23B, in which the second handling portion 2284 is in an elastically deflected configuration. In the second configuration, the second handling portion 2284 is deflected downward (with reference to the orientation of FIGS. 23A and 23B) relative to the main body portion of the staple retainer 2206, which presses the second handling portion 2284 against the stapler reload cartridge body 2201 as the first handling portion 2283 is pulled upward. This permits a force to be applied by the user to the stapler reload cartridge body 2201 toward the stapler reload cartridge body 2201 so as to help maintain the stapler reload cartridge body 2201 in the cartridge-retaining jaw 2260 as the staple retainer 2206 is pulled away with force R. As the second handling portion 2284 deflects and the staple retainer 2206 is pulled away and removed from the stapler reload cartridge body 2201, the septum 1644 (FIGS. 16B and 19) and projections 1678 (FIGS. 16B and 19) are fully disengaged from the stapler reload cartridge body 2201, and the stapler reload cartridge body 2201 remains seated in the cartridge-retaining jaw while the remaining portions of the stapler retainer 2206 are lifted away from the stapler reload cartridge body 2201 and the staple retainer 2206 is fully removed.

As one possible example of use, one or more fingers can be placed underneath (in the orientation of FIGS. 23A and 23B) the first handling portion 2283 to apply force R while a thumb can be used to press on the second handling portion 2284 to keep the stapler reload cartridge body 2201 seated in the cartridge-retaining jaw 2260. Other configurations or combinations can be used without limitation to apply forces R and T, such as using two hands with various combinations of fingers and thumbs or a mechanical apparatus to apply forces R and T.

The second handling portion 2284 can include various other features to facilitate handling and manipulation of the staple retainer 2206. For example, referring again to FIG. 22, the second handling portion 2284 comprises an aperture 2291 that can provide a seat for a thumb or finger and enhance the ability to grip the second handling portion 2284 when applying force T. In other embodiments, the second handling portion 2284 can include textured surfaces, such as a knurled surface, a pebbled surface, a ridged surface, crosshatched surface, or any other surface feature(s) to ensure sufficient friction between a thumb or finger and the second handling portion 2284 for application of force T. The embodiment of FIGS. 22-23B can include other features to further facilitate ease of handling.

Embodiments of the present disclosure discussed in connection with FIGS. 1-23B are generally discussed in connection with a stapler instrument that uses a single staple reload cartridge that installs in a cartridge-retaining jaw of the stapler instrument. However, some stapler instruments use multiple staple reload cartridges, such as two reload cartridges, one installed in each of two opposing jaws. One example of such an instrument is disclosed in Int'l Publication No. WO2020/081960 A1 (filed on 18 Oct. 2019) and titled "ENDOSCOPIC PURSE STRING SUTURE SURGICAL DEVICE."

Figure 24:
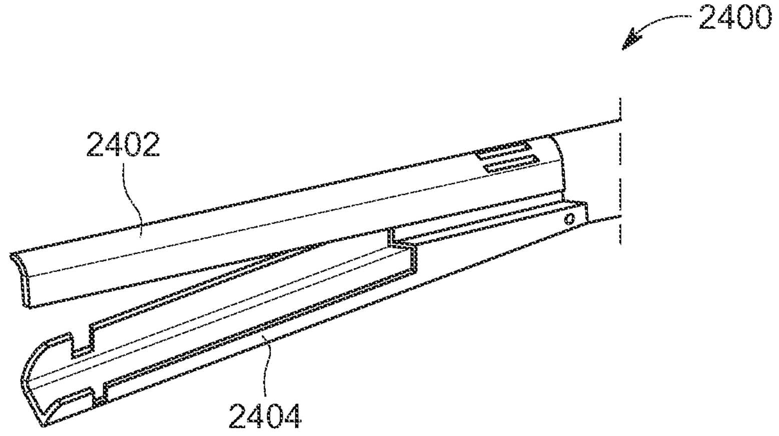
FIG. 24 is a perspective view of an end effector portion of a stapler instrument according to an embodiment of the present disclosure.

Referring now to FIG. 24, a stapler instrument 2400 having first and second jaws is shown. The stapler instrument 2400 includes first jaw 2402 and second jaw 2404 movable from an open position, as shown in FIG. 24, to a closed (e.g., clamped) position via movement of one or other of first jaw 2402 and second jaw 2404. Both first jaw 2402 and second jaw 2404 are configured to receive a stapler reload cartridge body. In some embodiments, the stapler reload cartridges are jaw-specific, with each jaw 2402 and 2404 respectively receiving a cartridge body unique from the other. Further, in some embodiments, the stapler reload cartridge bodies are coupled to one another by a length of suture material (e.g., for "purse string" type sutures inserted by instruments disclosed in publication WO2020/081960 A1 referenced above). While the embodiments of FIGS. 2-23B include a staple retainer on one side of the cartridge reload body and a removable cover on an opposite side of the cartridge reload body, the embodiments of FIGS. 24-27 do not include separate removable covers on the stapler reload cartridge bodies. However, a person of ordinary skill in the art will appreciate that such removable covers as those disclosed in connection with FIGS. 2-23B could be used in connection with the general embodiments disclosed in connection with FIGS. 24-27.

Figure 25:
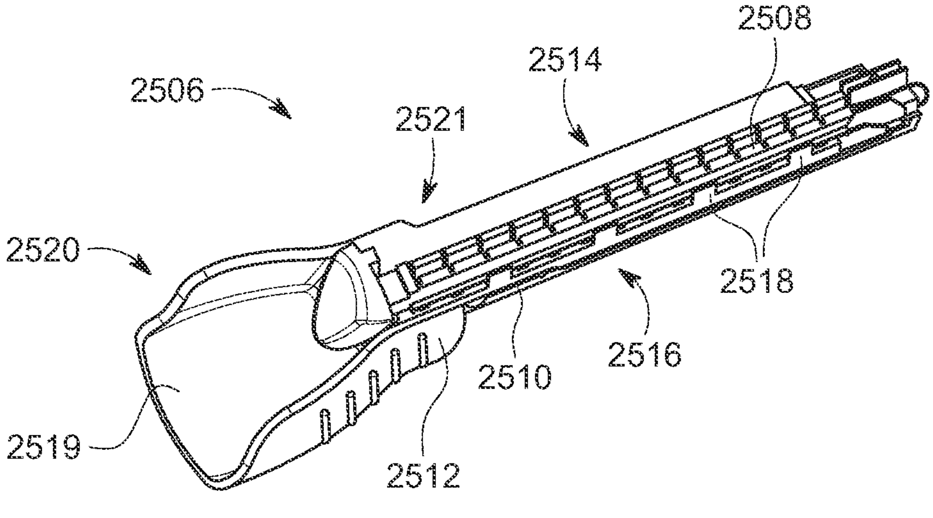
FIG. 25 is a perspective view of a stapler reload assembly according to another exemplary embodiment of the present disclosure.

To facilitate handling and installation of the multiple reload cartridge bodies and to prevent damage to the cartridge bodies, a plurality of cartridges, such as two cartridges, can be installed on a single staple retainer. Referring now to FIG. 25, an embodiment of a multiple cartridge stapler reload assembly 2506 is shown. The multiple cartridge stapler reload assembly 2506 includes a first reload cartridge body 2508 and a second reload cartridge body 2510 both coupled to a staple retainer 2512. In the embodiment of FIG. 25, the staple retainer 2512 has a first side 2514 and a second side 2516 generally opposite the first side 2514. In the orientation of FIG. 25, the first side 2514 is the top side and the second side 2516 is the bottom side. The first reload cartridge body 2508 is removably coupled to the first side 2514 and the second reload cartridge body 2510 is removably coupled to the second side 2516. The first reload cartridge body 2508 and second reload cartridge body 2510 can be coupled respectively to the first side 2514 and second side 2516 by any of the interacting features discussed in connection with other embodiments of reload assemblies disclosed herein. For example, the first reload cartridge body 2508 and second reload cartridge body 2510 can be coupled to the staple retainer 2512 by, for example, one or more protrusions on one of the reload cartridge body and the staple retainer and a corresponding one or more detents on the other of the reload cartridge body and the staple retainer. For example, the protrusions and detents can be configured similarly to the retention tabs 1434 and corresponding detents 1432 disclosed in connection with the embodiment of FIG. 15B. Other features such as septa with or without engagement tabs (for example, similar to septum 1644 with tabs 1676 disclosed in connection with FIG. 16B), other retention and alignment features, features that increase a required force to be applied to remove the cartridge bodies from the staple retainer, or other interacting features disclosed in combination with any of the embodiments herein can be used with the staple retainer and reload cartridge bodies of FIG. 25.

The staple retainer 2512 can include a plurality of retention features that engage one or the other of the first reload cartridge body 2508 and the second reload cartridge body 2510 to retain the first reload cartridge body 2508 and the second reload cartridge body 2510 on the staple retainer 2512. For example, in the embodiment of FIG. 25, the staple retainer 2512 includes a plurality of retention tabs 2518 that engage the first reload cartridge body 2508 via an interference fit to retain the staple retainer 2512 on the first reload cartridge body 2508. The staple retainer 2512 can include additional features that retain and/or position the first reload cartridge body 2508 and/or second reload cartridge body 2510 relative to the staple retainer 2512 and the instrument jaws, such as additional retention tabs (similar to retention tabs 2518) that engage the second reload cartridge body 2510.

The staple retainer 2512 can include various features configured to facilitate handling and installation of the multiple cartridge stapler reload assembly 2506. For example, referring still to FIG. 25, the staple retainer 2512 includes a handling portion 2520 extending from a distal end portion 2521 of the staple retainer 2512 and configured to be held during handling and/or installation of the multiple cartridge reload assembly. In the embodiment of FIG. 25, the handling portion 2520 comprises a generally paddle-shaped portion 2519 configured to be grasped by a user, e.g., between a thumb and forefinger. The handling portion 2520 further comprises laterally opposed gripping members 2522 and 2524 configured to provide an alternative gripping position, e.g., with the gripping members 2522 and 2524 between a thumb and finger.

Figure 26:
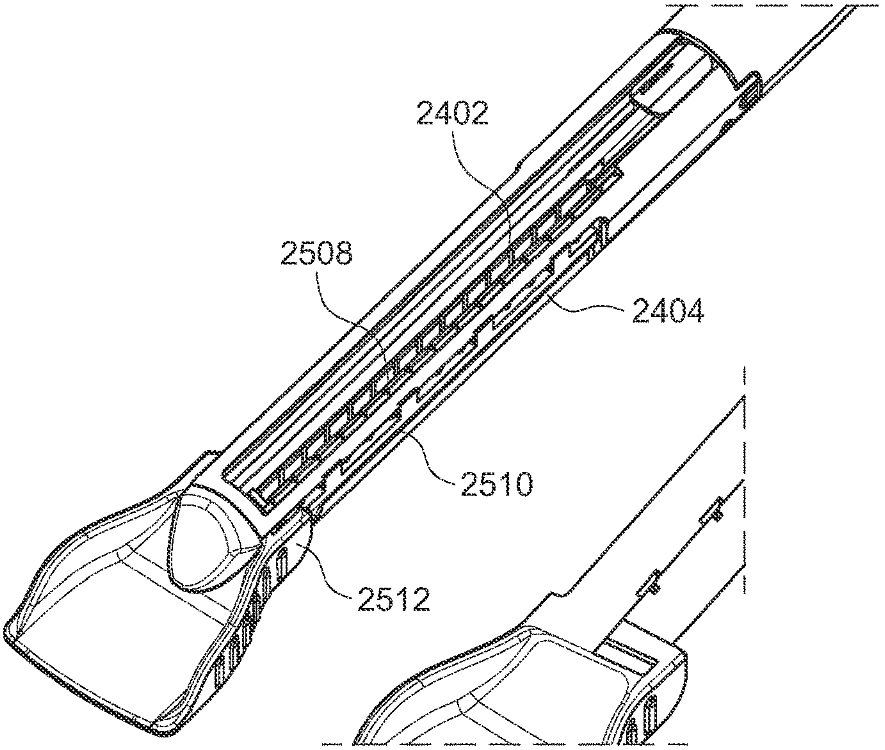
FIG. 26 is a perspective view of a stapler reload assembly installed on a stapler instrument according to an exemplary embodiment of the present disclosure.
Figure 27:
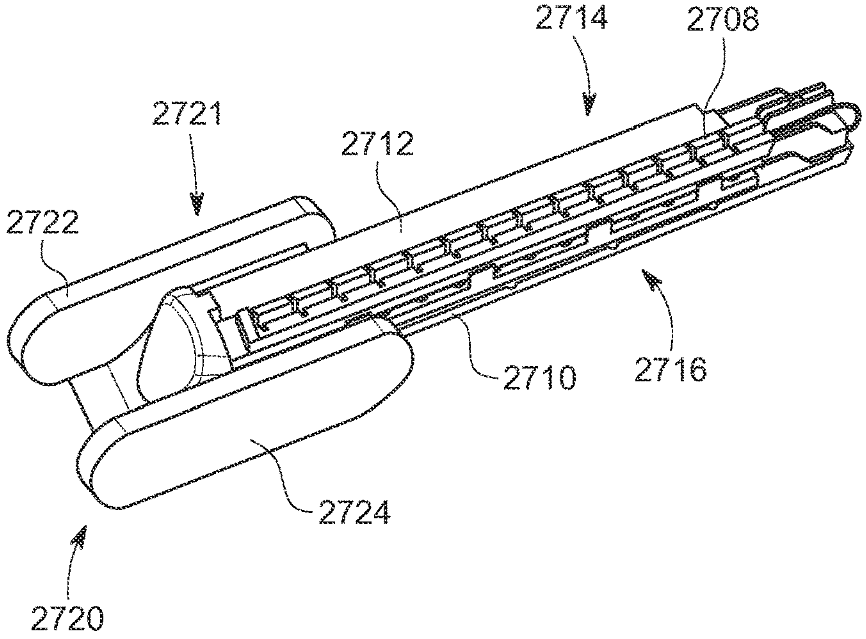
FIG. 27 is a perspective view of a stapler reload assembly according to yet another exemplary embodiment of the present disclosure.

To install the first and second reload cartridge bodies in the stapler instrument (e.g., stapler instrument 2400 in FIG. 24), the instrument jaws are opened and the staple retainer 2512 with first reload cartridge body 2508 and second reload cartridge body 2510 attached thereto is inserted between the instrument jaws. Using the handling portion 2520 to hold the staple retainer 2512, the first reload cartridge body 2508 and second reload cartridge body 2510 can be positioned between the jaws 2402 and 2404 and the jaws 2402, 2404 closed over the cartridges, as shown in FIG. 26. A retaining force holding the cartridges in the jaws may be greater than the retaining force provided by the interacting features of the first and second reload cartridge bodies and staple retainer, so that once the first and second reload cartridge bodies are installed in the respective first and second jaws, the jaws can be opened and the staple retainer can be pulled away from the reload cartridge bodies while the reload cartridge bodies remain engaged in the respective jaw.

The handling portion can have various configurations, each of which may be configured for ease of handling by the user and to avoid interference between the handling portion and the stapler instrument. For example, referring now to FIG. 27, another embodiment of a stapler reload assembly 2706 with a staple retainer 2712 is shown. The staple retainer 2712 is configured similarly to staple retainer 2512 (FIG. 25) with a first side 2714 and second side 2716. The staple retainer 2712 includes a handling portion 2720 positioned proximate a distal end portion 2721 of the staple retainer 2712. The handling portion 2720 comprises laterally opposed gripping members 2722 and 2724. The gripping members 2722 and 2724 are configured to be grasped during handling and/or installation of the multiple cartridge reload assembly. In exemplary embodiments, the gripping members 2722 and 2724 can have various configurations and features that facilitate grasping. For example, the gripping members 2722 and 2724 can have a generally concave surface profile to receive a finger or like member. Additionally or alternatively, the gripping members 2722 and 2724 can have a surface texture such as knurling, a pebbled texture, ridges, crosshatching, or other surface features configured to facilitate gripping of the gripping members 2722 and 2724. Further, while the gripping members 2722 and 2724 in the embodiment of FIG. 27 have concave surfaces, in other embodiments the gripping members 2722 and 2724 can be flat, convex, or have other shapes including combinations of shapes.

Embodiments of the present disclosure enable a stapler reload cartridge to have a relatively small size profile while still accommodating relatively large size staples. In addition, embodiments of the present disclosure are configured to provide an ordered manner to remove the cover and staple retainer components of the stapler reload assembly when installing the stapler reload cartridge body in a stapler instrument and readying it for subsequent use.

Instruments including the embodiments described herein may be used, for example, with teleoperated surgical systems that operate at least in part with computer assistance, such as the da Vinci® Surgical System, the da Vinci SI® Surgical System, the da Vinci X® Surgical System, the da Vinci Xi® Surgical System, or the da Vinci SP® Surgical System, all commercialized by Intuitive Surgical, Inc. of Sunnyvale, California. Although various embodiments described herein are discussed with regard to surgical instruments used with a manipulating system of a computer-assisted surgical system employing robotic technology, the present disclosure is not limited to use with surgical instruments for such surgical systems. For example, various embodiments described herein can optionally be used in conjunction with hand-held, manual or semi-automated surgical instruments, such as those used for manual laparoscopic surgery, or other surgical and non-surgical instruments.

This description and the accompanying drawings that illustrate exemplary embodiments should not be taken as limiting. Various mechanical, compositional, structural, electrical, and operational changes may be made without departing from the scope of this description and the invention as claimed, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with the following claims being entitled to their fullest breadth, including equivalents, under the applicable law.

What is claimed is:

1. A stapler reload assembly comprising:

a cartridge body defining a housing to receive staples, the cartridge body comprising a plurality of staple apertures configured to eject staples housed in the cartridge body; and a staple retainer removably coupled to the cartridge body;

wherein the staple retainer comprises:

a main body portion having a proximal end and a distal end, the main body portion configured to at least partially cover the plurality of staple apertures in a position of the staple retainer coupled to the cartridge body, a first handling portion extending distally from the main body portion and forming a distal end portion of the staple retainer, and a second handling portion coupled to the distal end of the main body portion by a flexure between and connected to the second handling portion and the distal end of the main body portion, the second handling portion having a length extending distally from the distal end of the main body portion to a distal, free end of the second handling portion, wherein the second handling portion is elastically deflectable about the flexure and relative to the main body portion of the staple retainer from a first, undeflected configuration to a second, deflected configuration, wherein the distal, free end of the second handling portion is configured to contact the cartridge body in the second, deflected configuration, and wherein, in a state of the staple retainer removably coupled to the cartridge body, the distal, free end of the second handling portion is accessible to a user to manipulate the second handling portion.

2. The stapler reload assembly of claim 1, wherein, on condition of a first force having a component in a first direction is applied at the first handling portion and a second force having a component in a second direction, opposite to the first direction, is applied to the second handling portion to elastically deflect the second handling portion about the flexure relative to the main body portion, the main body portion of the staple retainer is lifted away from the cartridge body.

3. The stapler reload assembly of claim 2, wherein the second force comprises a force applied to the second handling portion toward the cartridge body.

4. The stapler reload assembly of claim 2, wherein in the second, deflected configuration, the second force presses the distal, free end of the second handling portion on the cartridge body and maintains a position of the cartridge body as the main body portion of the staple retainer is lifted away from the cartridge body.

5. The stapler reload assembly of claim 1, wherein the flexure comprises a living hinge.

6. The stapler reload assembly of claim 1, wherein the staple retainer comprises one or more retaining features configured to interact with the cartridge body to retain the staple retainer on the cartridge body.

7. The stapler reload assembly of claim 6,
- wherein the one or more retaining features of the staple retainer comprise projections that engage a portion of the cartridge body, and
- wherein the projections are located and configured such that the projections are at least partially disengaged from the reload cartridge body by contact with a cartridge-retaining jaw of a stapler instrument in an installed position of the cartridge body in the cartridge-retaining jaw.

8. The stapler reload assembly of claim 1, wherein the cartridge body has a U-shape with legs extending longitudinally along the cartridge body and defining a central recess therebetween, and
- wherein the staple retainer comprises a septum extending into the central recess in an installed position of the staple retainer on the cartridge body.

9. The stapler reload assembly of claim 8, wherein the septum comprises one or more engagement tabs that engage a portion of the cartridge body in the installed position of the staple retainer on the cartridge body.

10. The stapler reload assembly of claim 1,
- wherein in the first, undeflected configuration, the second handling portion and main body are not angled relative to each other, and
- wherein in the second, deflected configuration, the second handling portion is deflected downward relative to the main body.

11. A stapler reload assembly comprising:
- a cartridge body defining a housing to receive staples, the cartridge body comprising:
  - a plurality of staple apertures on a first side of the cartridge body, the plurality of staple apertures configured to eject staples housed in the cartridge body;
  - a plurality of pusher apertures on a second side of the cartridge body opposite the first side, the plurality of pusher apertures configured to permit passage of staple pushers of the cartridge body;
- a cover removably coupled to the second side of the cartridge body and at least partially covering the plurality of pusher apertures;
- a staple retainer removably coupled to the first side of the cartridge body and engaged with the cover; wherein the staple retainer comprises:
  - a main body portion configured to at least partially cover the plurality of staple apertures in a position of the staple retainer coupled to the cartridge body;
  - a first handling portion extending from the main body portion at a distal end portion of the staple retainer; and
  - a second handling portion proximal the first handling portion and coupled to the main body portion by a flexure, wherein the second handling portion is elastically deflectable about the flexure and relative to the main body portion of the staple retainer from a neutral, first position to a deflected, second position,
- wherein in a coupled state of the staple retainer and the cover with the cartridge body, removal of the staple retainer from the cartridge body prior to removal of the cover from the cartridge body is prevented, and
- wherein the staple retainer and the cover are disengageable from each other upon sequential removal of the cover followed by the staple retainer from the cartridge body.

12. The stapler reload assembly of claim 11, wherein one or both of the cover and the cartridge body comprise retaining features configured to retain the cover on the cartridge body.

13. A method of installing a reload cartridge body in a stapler instrument, the method comprising:
- inserting the reload cartridge body in a jaw of the stapler instrument while a staple retainer is coupled to the reload cartridge body with a main body portion of the staple retainer at least partially covering a plurality of staple apertures of the reload cartridge body;
- while the reload cartridge body is inserted in the jaw of the stapler instrument, applying a first force to a first handling portion forming a distal end portion of the staple retainer, the first force applied in a direction to lift the staple retainer from the reload cartridge body;
- while applying the first force, applying a second force to a second handling portion, the second handling portion coupled to the main body portion by a flexure between and connected to the second handling portion and the main body portion, the second handling portion having a length extending distally from a distal end of the main body portion to a distal, free end of the second handling portion, the second force applied in a direction to move and press the distal, free end of the second handling portion against the reload cartridge body toward the jaw of the stapler instrument; and
- in response to applying the first force and the second force, elastically deflecting the second handling portion about the flexure and relative to the main body of the staple retainer from a first, undeflected configuration to a second, deflected configuration.

14. The method of claim 13, wherein the first force comprises a component in a first direction and the second force comprises a component in a second direction generally opposite the first direction.

15. The method of claim 13, wherein in the second, deflected configuration, the second handling portion pressing on the reload cartridge body maintains a position of the reload cartridge body in the jaw of the stapler instrument, and the first force is sufficient to lift the retainer away from the reload cartridge body.

16. The method of claim 13, further comprising:

prior to inserting the reload cartridge body in the jaw of the stapler instrument, removing a cover from a side of the reload cartridge body opposite a side the staple retainer.

17. The method of claim 16, wherein the cover and the staple retainer engage with each other while on the reload cartridge body such that the cover prevents removal of the staple retainer from the reload cartridge body prior to removal of the cover from the reload cartridge body.

18. The method of claim 13, wherein elastically deflecting the second handling portion about the flexure from a first, undeflected configuration to a second, deflected configuration comprises deflecting the second handling portion downward relative to the main body portion.

* * * * *